United States Patent
Doxey

(10) Patent No.: US 11,077,194 B2
(45) Date of Patent: Aug. 3, 2021

(54) NITRIC OXIDE RELEASING PHARMACEUTICAL COMPOSITIONS

(71) Applicant: Novan, Inc., Durham, NC (US)

(72) Inventor: Ryan Doxey, Raleigh, NC (US)

(73) Assignee: Novan, Inc., Durham, NC (US)

( * ) Notice: Subject to any disclaimer, the term of this patent is extended or adjusted under 35 U.S.C. 154(b) by 0 days.

(21) Appl. No.: 14/381,370

(22) PCT Filed: Feb. 28, 2013

(86) PCT No.: PCT/US2013/028223
§ 371 (c)(1),
(2) Date: Aug. 27, 2014

(87) PCT Pub. No.: WO2013/138075
PCT Pub. Date: Sep. 19, 2013

(65) Prior Publication Data
US 2015/0024052 A1    Jan. 22, 2015

Related U.S. Application Data

(60) Provisional application No. 61/610,563, filed on Mar. 14, 2012.

(51) Int. Cl.
| | | |
|---|---|---|
| A61K 47/32 | (2006.01) | |
| A61K 45/06 | (2006.01) | |
| A61L 26/00 | (2006.01) | |
| A61K 9/00 | (2006.01) | |
| A61K 33/00 | (2006.01) | |
| A61K 47/10 | (2017.01) | |
| A61K 47/12 | (2006.01) | |
| A61K 47/14 | (2017.01) | |
| A61K 47/26 | (2006.01) | |
| A61K 47/34 | (2017.01) | |
| A61K 47/38 | (2006.01) | |
| A61K 47/44 | (2017.01) | |

(52) U.S. Cl.
CPC ............ *A61K 47/32* (2013.01); *A61K 9/0014* (2013.01); *A61K 33/00* (2013.01); *A61K 45/06* (2013.01); *A61K 47/10* (2013.01); *A61K 47/12* (2013.01); *A61K 47/14* (2013.01); *A61K 47/26* (2013.01); *A61K 47/34* (2013.01); *A61K 47/38* (2013.01); *A61K 47/44* (2013.01); *A61L 26/0004* (2013.01); *A61L 26/0019* (2013.01); *A61L 26/0061* (2013.01); *A61L 26/0066* (2013.01); *A61L 26/0095* (2013.01); *A61L 2300/114* (2013.01); *A61L 2300/22* (2013.01)

(58) Field of Classification Search
CPC ........ A61K 45/06; A61K 47/26; A61K 47/32; A61K 47/10; A61K 47/12; A61K 47/14; A61K 33/10; A61K 9/0014; A61K 47/44; A61K 47/34; A61K 47/38
See application file for complete search history.

(56) References Cited

U.S. PATENT DOCUMENTS

| | | |
|---|---|---|
| 4,917,866 A | 4/1990 | Abe et al. |
| 5,968,528 A | 10/1999 | Deckner et al. |
| 6,103,266 A | 8/2000 | Tapolsky et al. |
| 6,319,913 B1 | 11/2001 | Mak et al. |
| 6,479,058 B1 | 11/2002 | McCadden |
| 7,704,518 B2 | 4/2010 | Tamarkin et al. |
| 8,241,650 B2 | 8/2012 | Peters |
| 8,282,967 B2 | 10/2012 | Schoenfisch et al. |
| 8,343,945 B2 | 1/2013 | Tamarkin et al. |
| 8,362,091 B2 | 1/2013 | Tamarkin et al. |
| 8,399,005 B2 | 3/2013 | Schoenfisch et al. |
| 8,486,374 B2 | 7/2013 | Tamarkin et al. |
| 8,591,876 B2 | 11/2013 | Bauman et al. |
| 8,617,100 B2 | 12/2013 | Eini et al. |
| 8,636,982 B2 | 1/2014 | Tamarkin et al. |
| 8,795,635 B2 | 8/2014 | Tamarkin et al. |
| 8,795,693 B2 | 8/2014 | Tamarkin et al. |
| 8,900,553 B2 | 12/2014 | Tamarkin et al. |
| 8,937,143 B2 | 1/2015 | Bao et al. |
| 8,956,658 B2 | 2/2015 | Schoenfisch et al. |
| 8,962,029 B2 | 2/2015 | Schoenfisch et al. |
| 8,981,139 B2 | 3/2015 | Schoenfisch et al. |
| 9,101,662 B2 | 8/2015 | Tamarkin et al. |
| 9,161,916 B2 | 10/2015 | Tamarkin et al. |
| 9,187,501 B2 | 11/2015 | Schoenfisch et al. |
| 9,238,038 B2 | 1/2016 | Schoenfisch et al. |
| 9,265,725 B2 | 2/2016 | Tamarkin et al. |
| 9,289,442 B2 | 3/2016 | Doxey et al. |
| 9,320,705 B2 | 4/2016 | Tamarkin et al. |
| 9,381,381 B2 | 7/2016 | Benjamin |
| 9,427,605 B2 | 8/2016 | Peters |
| 9,669,041 B2 | 6/2017 | Stasko et al. |

(Continued)

FOREIGN PATENT DOCUMENTS

| | | |
|---|---|---|
| CN | 101732728 | 6/2010 |
| CN | 101791411 | 8/2010 |

(Continued)

OTHER PUBLICATIONS

Choi et al., WO 2010/016686, published: Feb. 2010; English Machine translation obtained on Apr. 15, 2016.*
Choi et al. WO 2010/016686, published: Feb. 11, 2010, English machine translation obtained on Sep. 10, 2020. (Year: 2010).*
International Search Report and the Written Opinion of the International Searching Authority corresponding to International Application No. PCT/US2013/028223; dated May 14, 2013, 9 pages.

(Continued)

*Primary Examiner* — Genevieve S Alley

(74) *Attorney, Agent, or Firm* — Myers Bigel, P.A.

(57) ABSTRACT

The present invention generally relates to nitric oxide releasing pharmaceutical compositions and methods of using the same.

22 Claims, 8 Drawing Sheets

(56) References Cited

U.S. PATENT DOCUMENTS

| | | |
|---|---|---|
| 9,757,397 B2 | 9/2017 | Kougoulos et al. |
| 9,855,211 B2 | 1/2018 | Doxey et al. |
| 10,206,947 B2 | 2/2019 | Doxey et al. |
| 10,258,564 B2 | 4/2019 | Doxey et al. |
| 10,322,081 B2 | 6/2019 | McHale et al. |
| 2002/0013304 A1 | 1/2002 | Wilson et al. |
| 2002/0028223 A1 | 3/2002 | Vatter et al. |
| 2005/0038473 A1 | 2/2005 | Tamarkin et al. |
| 2005/0232869 A1 | 10/2005 | Tamarkin et al. |
| 2005/0271596 A1 | 12/2005 | Friedman et al. |
| 2006/0160897 A1 | 7/2006 | Pelicci et al. |
| 2006/0275218 A1 | 12/2006 | Tamarkin et al. |
| 2007/0166255 A1 | 7/2007 | Gupta |
| 2007/0292359 A1 | 12/2007 | Friedman et al. |
| 2007/0292461 A1 | 12/2007 | Tamarkin et al. |
| 2008/0031907 A1 | 2/2008 | Tamarkin et al. |
| 2008/0044444 A1 | 2/2008 | Tamarkin et al. |
| 2008/0063607 A1 | 3/2008 | Tamarkin et al. |
| 2008/0069779 A1 | 3/2008 | Tamarkin et al. |
| 2008/0071206 A1 | 3/2008 | Peters |
| 2008/0138296 A1 | 6/2008 | Tamarkin et al. |
| 2008/0152596 A1 | 6/2008 | Friedman et al. |
| 2008/0166303 A1 | 7/2008 | Tamarkin et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0253973 A1 | 10/2008 | Tamarkin et al. |
| 2008/0260655 A1 | 10/2008 | Tamarkin et al. |
| 2008/0292560 A1 | 11/2008 | Tamarkin et al. |
| 2008/0311163 A1 | 12/2008 | Peters |
| 2008/0317679 A1 | 12/2008 | Tamarkin et al. |
| 2009/0041680 A1 | 2/2009 | Tamarkin et al. |
| 2009/0068118 A1 | 3/2009 | Eini et al. |
| 2009/0130029 A1 | 5/2009 | Tamarkin et al. |
| 2009/0175799 A1 | 7/2009 | Tamarkin et al. |
| 2009/0214618 A1* | 8/2009 | Schoenfisch et al. ........ 424/426 |
| 2009/0297634 A1 | 12/2009 | Friedman et al. |
| 2010/0098733 A1 | 4/2010 | Stasko et al. |
| 2010/0221195 A1 | 9/2010 | Tamarkin et al. |
| 2010/0266510 A1 | 10/2010 | Tamarkin et al. |
| 2010/0286285 A1* | 11/2010 | Barthez ................ A61K 9/0014 514/721 |
| 2010/0310476 A1 | 12/2010 | Tamarkin et al. |
| 2011/0045037 A1 | 2/2011 | Tamarkin et al. |
| 2011/0086234 A1 | 4/2011 | Stasko et al. |
| 2011/0097279 A1 | 4/2011 | Tamarkin et al. |
| 2011/0212033 A1 | 9/2011 | Tamarkin et al. |
| 2012/0134951 A1 | 5/2012 | Stasko et al. |
| 2012/0136323 A1 | 5/2012 | Stasko et al. |
| 2012/0141384 A1 | 6/2012 | Tamarkin et al. |
| 2012/0237453 A1 | 9/2012 | Tamarkin et al. |
| 2013/0164225 A1 | 6/2013 | Tamarkin et al. |
| 2013/0189191 A1 | 7/2013 | Tamarkin et al. |
| 2013/0189193 A1 | 7/2013 | Tamarkin et al. |
| 2013/0189195 A1 | 7/2013 | Tamarkin et al. |
| 2013/0310533 A1 | 11/2013 | Bao et al. |
| 2013/0344334 A1 | 12/2013 | Schoenfisch et al. |
| 2014/0134321 A1 | 5/2014 | Stasko et al. |
| 2014/0193502 A1 | 7/2014 | Tamarkin et al. |
| 2014/0248219 A1 | 9/2014 | Tamarkin et al. |
| 2014/0271494 A1 | 9/2014 | Tamarkin et al. |
| 2014/0369949 A1 | 12/2014 | Peters |
| 2015/0017103 A1 | 1/2015 | Tamarkin et al. |
| 2015/0024052 A1 | 1/2015 | Doxey |
| 2015/0025060 A1 | 1/2015 | Tamarkin et al. |
| 2015/0111973 A1 | 4/2015 | Bauman et al. |
| 2015/0118164 A1 | 4/2015 | Tamarkin et al. |
| 2016/0106657 A9 | 4/2016 | Peters |
| 2016/0199295 A1 | 7/2016 | Doxey et al. |
| 2017/0196905 A1 | 7/2017 | Doxey et al. |
| 2018/0200541 A1 | 7/2018 | Doxey et al. |
| 2018/0319822 A1 | 11/2018 | Schoenfisch et al. |

FOREIGN PATENT DOCUMENTS

| | | |
|---|---|---|
| EP | 1 707 224 A1 | 10/2006 |
| EP | 1 861 130 B1 | 9/2008 |
| EP | 1 871 433 B1 | 4/2009 |
| EP | 1 846 058 B1 | 7/2009 |
| EP | 2 119 459 A1 | 11/2009 |
| EP | 2 142 179 A1 | 1/2010 |
| EP | 2 142 181 A1 | 1/2010 |
| EP | 1 917 005 B1 | 9/2010 |
| JP | 03-044396 | 2/1991 |
| JP | 2003-212773 | 7/2003 |
| WO | 9944622 | 9/1999 |
| WO | 01021148 | 3/2001 |
| WO | 03/09539 | 11/2003 |
| WO | WO 2005/004984 A1 | 1/2005 |
| WO | WO 2006/084910 A2 | 8/2006 |
| WO | WO 2006/084912 A1 | 8/2006 |
| WO | WO 2006/100154 A1 | 9/2006 |
| WO | WO 2007/007208 A2 | 1/2007 |
| WO | WO 2007/023005 A1 | 3/2007 |
| WO | WO 2007/023396 A2 | 3/2007 |
| WO | WO 2007/054818 A2 | 5/2007 |
| WO | WO 2008/032212 A2 | 3/2008 |
| WO | WO 2008/038140 A2 | 4/2008 |
| WO | WO 2008/038147 A2 | 4/2008 |
| WO | WO 2008/094866 A1 | 8/2008 |
| WO | WO 2008/110872 A2 | 9/2008 |
| WO | WO 2008/116497 A1 | 10/2008 |
| WO | WO 2008/116925 A1 | 10/2008 |
| WO | WO 2008/152444 A2 | 12/2008 |
| WO | WO 2009/007785 A2 | 1/2009 |
| WO | WO 2009/049208 A1 | 4/2009 |
| WO | WO 2009/056991 A2 | 5/2009 |
| WO | WO 2009/072007 A2 | 6/2009 |
| WO | WO 2009/087578 A2 | 7/2009 |
| WO | WO 2009/090495 A2 | 7/2009 |
| WO | WO 2009/098595 A2 | 8/2009 |
| WO | WO 2009/131931 A1 | 10/2009 |
| WO | WO 2010/016686 * | 2/2010 |
| WO | 2010044875 | 4/2010 |
| WO | WO 2011/005846 A1 | 1/2011 |
| WO | WO 2011 022652 * | 2/2011 |
| WO | WO 2011/022652 A1 | 2/2011 |
| WO | WO 2011/022680 A2 | 2/2011 |
| WO | 2011047013 | 4/2011 |
| WO | WO 2011/061519 A2 | 5/2011 |
| WO | 2011085484 | 7/2011 |
| WO | WO2012001403 * | 1/2012 |
| WO | 2012035468 A2 | 3/2012 |
| WO | 2012082976 | 6/2012 |
| WO | 2012100174 | 7/2012 |
| WO | 2012118829 | 7/2012 |
| WO | 2012118819 | 9/2012 |
| WO | 2013006613 | 1/2013 |
| WO | WO 2013/006608 A1 | 1/2013 |
| WO | 2013029009 | 2/2013 |
| WO | 2013063354 | 5/2013 |
| WO | 2013138073 | 9/2013 |
| WO | 2013138075 | 9/2013 |
| WO | 2014028847 | 2/2014 |
| WO | 2014134502 | 9/2014 |
| WO | 2015021382 | 2/2015 |
| WO | 2016007834 | 1/2016 |
| WO | 2016010988 | 1/2016 |
| WO | 2016022170 | 2/2016 |
| WO | 2016160089 | 10/2016 |
| WO | 2017011031 | 1/2017 |
| WO | 2017019614 | 2/2017 |
| WO | 2017151905 | 9/2017 |
| WO | 2017180822 | 10/2017 |
| WO | 2018189887 | 10/2018 |
| WO | 2018236806 | 12/2018 |

(56) References Cited

FOREIGN PATENT DOCUMENTS

| WO | 2019169221 | 9/2019 |
|---|---|---|
| WO | 2019232166 | 12/2019 |

OTHER PUBLICATIONS

International Preliminary Report on Patentability Corresponding to International Application No. PCT/US2013/028223; dated Sep. 16, 2014.

Amadeu et al. "Nitric Oxide Donor Improves Healing if Applied on Inflammatory and Proliferative Phase" *Journal of Surgical Research* 149(1):84-93 (2008).

Bohl Masters et al. "Effects of nitric oxide releasing poly(vinyl alcohol) hydrogel dressings on dermal wound healing in diabetic mice" *Wound Repair and Regeneration* 10(5):286-294 (2002).

Hetrick et al. "Anti-biofilm efficacy of nitric oxide-releasing silica nanoparticles" *Biomaterials* 30(14):2782-2789 (2009).

Chinese Office Action corresponding to Chinese Patent Application No. 201380014039.2 (22 pages) (dated Sep. 22, 2015).

Extended European Search Report corresponding to European Patent Application No. 13761286.7 (6 pages) (dated Nov. 2, 2015).

Boykin et al. "HBO Mediates Increased Nitric Oxide Production Associated With Wound Healing" *Wound Repaid and Regeneration* 12(2):A15 (Abstract 054) (2004).

Office Action corresponding to Japanese Patent Application No. 2015-500453 (7 pages) (dated Dec. 6, 2016).

Office Action corresponding to Chinese Patent Application No. 201380014039.2 (9 pages) (dated Jul. 27, 2016).

Examination Report corresponding to European Patent Application No. 13761286.7 (8 pages) (dated Oct. 30, 2017).

Keefer, Larry K. "Fifty Years of Diazeniumdiolate Research. From Laboratory Curiosity to Broad-Spectrum Biomedical Advances" *ACS Chemical Biology*, 6:1147-1155 (2011).

\* cited by examiner

NITRIC OXIDE RELEASING PHARMACEUTICAL COMPOSITIONS

RELATED APPLICATION DATA

This application is a 35 § 371 national stage application of International Application No. PCT/US2013/028223, filed on Feb. 28, 2013, which claims the benefit of U.S. Provisional Patent Application Ser. No. 61/610,563, filed Mar. 14, 2012, the disclosures of which are incorporated herein by reference in their entirety.

FIELD OF THE INVENTION

The present invention generally relates to nitric oxide releasing pharmaceutical compositions and methods of using the same.

BACKGROUND OF THE INVENTION

Numerous skin diseases or disorders result from inflammation with the associated release of mediators from a variety of inflammatory and resident cells. Neutrophils, mast cells and lymphocytes orchestrate an inflammatory response that results in significant release of inflammatory mediators, and the creation of numerous free radicals. Skin diseases in which inflammation is a significant component include, but are not limited to, acne and rosacea, atopic dermatitis, contact dermatitis, drug eruptions, psoriasis, seborrheic dermatitis, connective tissue diseases (such as lupus and scleroderma), other autoimmune disorders such as the blistering disease bullous pemphigoid or pemphigus, pigmentary diseases (such as post inflammatory hyperpigmentation, melasma and vitiligo), urticaria or hives, inflammation associated with skin infections such as tinea corporis or fungal infection of the finger or toenails, among others. Inflammation is an important step to most of these diseases. New compositions for treating inflammatory skin conditions and methods of making and/or using such compositions may be desirable.

Similarly, many wounds, chronic or acute, may have inflammatory aspects. In inflammatory conditions and wounds, delivery of a therapeutic agent should be provided without substantial irritation or exacerbation of the inflammatory condition. Furthermore, if the active ingredient is moisture activated, aqueous vehicles may be inappropriate. Mineral oil ointments alone may protect the moisture activate agent from moisture prior to application but they may also reduce the effectiveness of the active agent at the time of application. Accordingly, new compositions for the delivery of moisture activated active agents and, in some cases, suitable for use in treating indications with an inflammatory aspect to the disease.

The present invention addresses previous shortcomings in the art by providing nitric oxide releasing pharmaceutical compositions and methods of using the same.

SUMMARY OF THE INVENTION

A first aspect of the present invention comprises a pharmaceutical composition for topical delivery of a moisture activated active pharmaceutical ingredient, the composition comprising: a hydrophobic base and an amphiphilic compound.

A second aspect of the present invention comprises a pharmaceutical composition for topical delivery of a moisture activated active pharmaceutical ingredient, the composition comprising: a moisture activated active pharmaceutical ingredient present in the composition at a concentration from about 0.1% to about 35%; a hydrophobic polymer present in the composition at a concentration from about 30% to about 60%; a mineral oil present in the composition at a concentration from about 1% to about 30%; an amphiphilic compound present in the composition at a concentration from about 1% to about 20%; a cosolvent present in the composition at a concentration from about 1% to about 25%; and a humectant present in the composition at a concentration from about 1% to about 25%.

A further aspect of the present invention comprises a method of treating the skin of a subject, the method comprising topically administering a pharmaceutical composition of the present invention in an amount effective to treat the skin of a subject.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

BRIEF DESCRIPTION OF THE DRAWINGS

The following drawings are provided to illustrate various aspects of the present inventive concept and are not intended to limit the scope of the present invention unless specified herein.

DETAILED DESCRIPTION OF THE INVENTION

Figure 1:
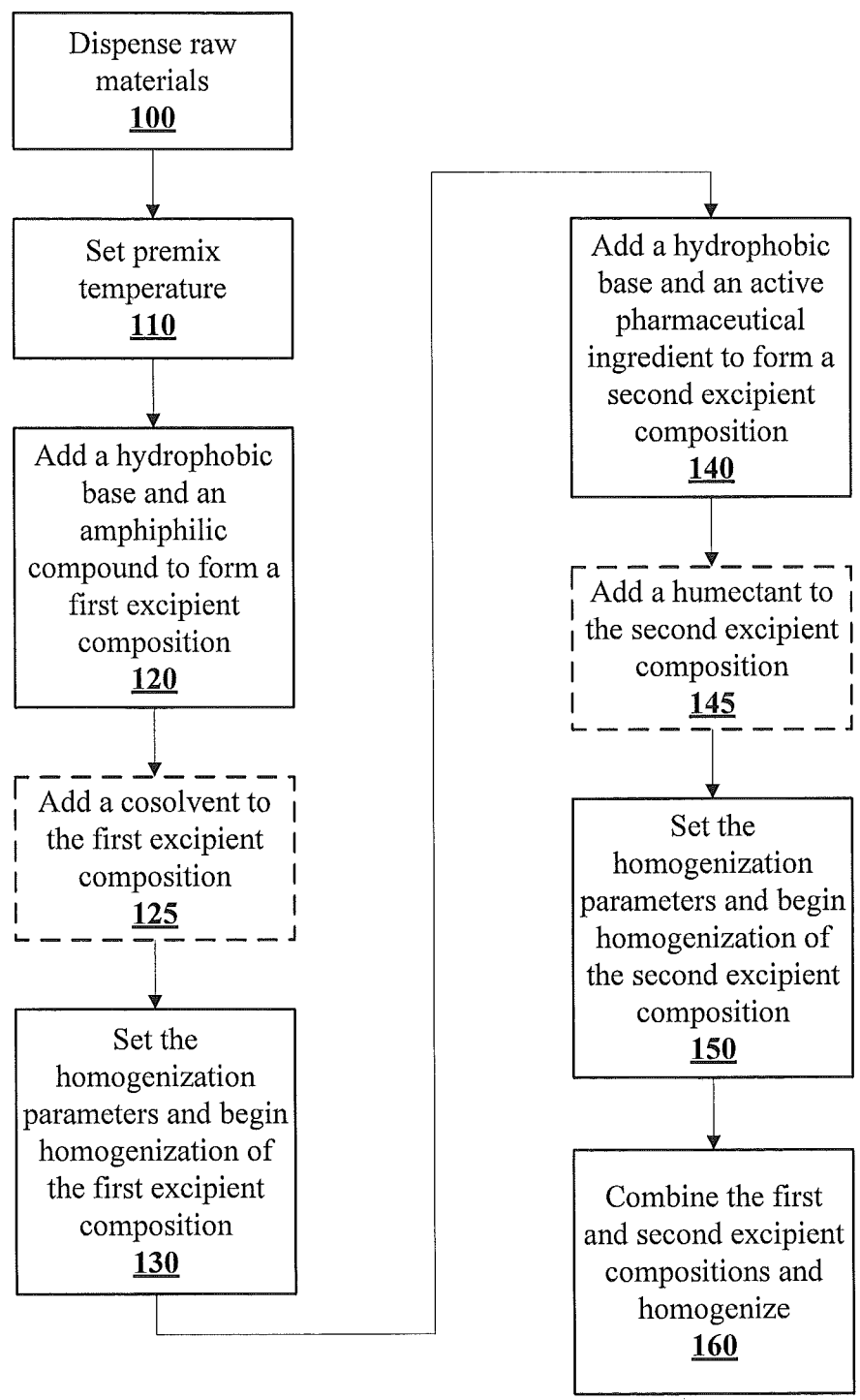
FIG. 1 shows a flowchart of operations for preparing a pharmaceutical composition according to some embodiments of the present invention.

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In the event of conflicting terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value such as an amount or concentration of a compound, dose, time, temperature, and the like, is meant to encompass variations of ±20%, ±10%, ±5%, ±1%, ±0.5%, or even ±0.1% of the specified amount. A range provided herein for a measurable value may include any other range and/or individual value therein.

The present invention provides pharmaceutical compositions that may be administered topically. A pharmaceutical composition of the present invention may comprise, consist essentially of, or consist of a hydrophobic base and an amphiphilic compound. In particular embodiments of the present invention, a pharmaceutical composition further comprises a moisture activated active pharmaceutical ingredient. A pharmaceutical composition of the present invention may comprise an ointment, salve, cream, and/or the like.

"Hydrophobic base" as used herein refers to a natural and/or synthetic fat, wax, oil, and/or the like. Any suitable hydrophobic base may be used in a pharmaceutical composition of the present invention. In certain embodiments of the present invention, a pharmaceutical composition comprises two or more hydrophobic bases, such as, but not limited to, 2, 3, 4, 5, or more hydrophobic bases. Exemplary hydrophobic bases include, but are not limited to, branched and unbranched hydrocarbons, branched and unbranched hydrocarbon waxes, vaseline, hydrocarbon gel, liquid paraffin, white petrolatum, petrolatum, microcrystalline wax, andelilla wax, carnauba wax, lanolin (wool wax), wool wax alcohol, esparto grass wax, cork wax, guaruma wax, rice bran wax, sugar cane wax, berry wax, ouricury wax, soy wax, jojoba oil, uropygial grease, ceresine, paraffin waxes, micro waxes, plant oils, animal oils, carnauba wax, beeswax, cacao butter, hard fat, mineral oil, vegetable oil, avocado oil, borage oil, canola oil, castor oil, chamomile oil, coconut oil, corn oil, cottonseed oil, rapeseed oil, evening primrose oil, safflower oil, sunflower oil, soybean oil, sweet almond, palm oil, palm kernel oil, arctium lappa seed oil, sesame oil, borgo officialis seed oil, brassica campestris oleifera oil, brevoortia oil, bubulum oil, cistus ladaniferus oil, *Elaeis guineensis* oil, almond oil, pine oil, olive oil, peanut oil, wheat germ oil, grape seed oil, thistle oil, lard, tallow, palm olein, illipe butter, shea butter, cocoa butter, kokum butter, sal butter, lecithin, japan wax lanolin, partially hydrogenated vegetable oils, hydrophobic polymers, and any combination thereof.

In some embodiments of the present invention, a hydrophobic base may comprise a hydrophobic polymer. Any suitable hydrophobic polymer may be used in a pharmaceutical composition of the present invention. Exemplary hydrophobic polymers include, but are not limited to hydrocarbon polymers and/or co-polymers, aromatic polyurethanes, silicone rubber, polysiloxanes, polycaprolactone, polycarbonate, polyvinylchloride, polyethylene, poly-L-lactide, poly-DL-glycolide, polyetheretherketone (PEEK), polyamide, polyimide and polyvinyl acetate. In particular embodiments of the present invention, a pharmaceutical composition of the present invention comprises one or more hydrocarbon polymers and/or co-polymers. In certain embodiments, a pharmaceutical composition of the present invention comprises one or more hydrocarbon polymers and/or co-polymers, such as, but not limited to, those commercially available from Calumet Specialty Products Partners of Indianapolis, Ind. under the trademark Versagel® and/or those commercially available from Croda International Plc of East Yorkshire, United Kingdom under the trade name Crodabase SQ.

In some embodiments of the present invention, a hydrophobic polymer may act as thickening and/or gelling agent in a pharmaceutical composition. Specifically, a hydrophobic polymer may act as a visco-elastic substance and may retain the composition at the site of application, along with any compounds dispersed therein (e.g., an active pharmaceutical ingredient, etc.). A hydrophobic polymer may be present in a pharmaceutical composition of the present invention at a concentration from about 30% to about 60% by weight or any range therein, such as, but not limited to, from about 35% to about 55% by weight or about 40% to about 50% by weight.

In particular embodiments of the present invention, a hydrophobic base comprises one or more plant and/or mineral oils. Any suitable oil may be used in the pharmaceutical compositions of the present invention. Exemplary mineral oils include, but are not limited to, light mineral oil, white mineral oil, paraffinic oils, napthenic oils, aromatic oils, and any combination thereof. An oil (e.g., plant and/or mineral oil) may be present in a pharmaceutical composition of the present invention at a concentration from about 1% to about 30% by weight or any range therein, such as, but not limited to, from about 5% to about 20% by weight or about 5% to about 15% by weight.

In some embodiments of the present invention, a hydrophobic base, such as, but not limited to, an oil (e.g., a plant and/or mineral oil), may be used to tune the viscosity and/or spreadability of the pharmaceutical composition. For example, a low viscosity hydrophobic base, such as light mineral, may be used to thin (i.e., reduce the viscosity) a pharmaceutical composition, such as, a pharmaceutical composition comprising a high viscosity hydrophobic base. This may enable the application of a pharmaceutical composition of the present invention over a wide area, and may serve to maintain any compounds dispersed therein (e.g., an active pharmaceutical ingredient, etc.) at the site of application. In certain embodiments of the present invention, a hydrophobic base comprises a mineral oil and a hydrophobic polymer.

A hydrophobic base may be present in a pharmaceutical composition of the present invention at a concentration from about 35% to about 90% by weight or any range therein, such as, but not limited to, from about 40% to about 80% by weight or about 50% to about 70% by weight. In certain embodiments of the present invention, a hydrophobic base is present in a pharmaceutical composition of the present invention at a concentration from about 45% to about 55% by weight.

"Amphiphilic compound" as used herein refers to a compound comprising hydrophilic and hydrophobic properties. An amphiphilic compound may comprise two or more compounds, each of which may provide the hydrophilic property and/or the hydrophobic property. In some embodiments, the amphiphilic compound comprises one compound having hydrophilic and hydrophobic properties. In particular embodiments of the present invention, an amphiphilic compound may absorb moisture without substantially absorbing vaporous moisture. The absorption of moisture may allow for activation of a moisture activated active pharmaceutical ingredient in a pharmaceutical composition of the present invention upon contact with the moisture, but not upon contact with vaporous moisture. "Substantially absorbing" (and grammatical variations thereof) as used herein means that the amount of vaporous moisture absorbed is more than 2% by weight of an amphiphilic compound. Thus, an amphiphilic compound of the present invention absorbs vaporous moisture by less than about 2%, 1.5%, 1%, 0.5%, 0.25% by weight of an amphiphilic compound or any range therein. In some embodiments of the present invention, an amphiphilic compound may prevent and/or minimize a pharmaceutical composition of the present invention from substantially absorbing vaporous moisture, thereby moisture may be present in a pharmaceutical composition of the present invention by less than about 2%.

"Moisture" as used herein refers to a liquid, such as, but not limited to, a bodily fluid such as, but not limited to, blood, sweat, mucus, saliva, sebum, tears, exudate, and/or vaginal secretions; water; deoxygenated water; saline solutions; acidic or alkaline buffer solutions; and/or any combination thereof. "Vaporous moisture" as used herein refers to moisture in the gas phase. For example, vaporous moisture, includes, but is not limited to, water vapor. Thus, in some embodiments of the present invention, an amphiphilic compound may prevent and/or minimize the absorption of water vapor, thereby, when the active pharmaceutical ingredient (API) comprises a moisture activated pharmaceutical ingredient, the API in a pharmaceutical composition of the present invention is not activated by the vaporous moisture (e.g., water vapor). In contrast, an amphiphilic compound may absorb and/or allow moisture (e.g., water, a bodily fluid, etc.) to be absorbed when a pharmaceutical composition of the present invention is contacted with the moisture, thereby activating the API when the API comprises a moisture activated active pharmaceutical ingredient.

In particular embodiments of the present invention, an amphiphilic compound absorbs water vapor by less than about 2% by weight or about 1% by weight. This may minimize and/or prevent a pharmaceutical composition of the present invention from absorbing water vapor and thus water may be present in a pharmaceutical composition of the present invention by less than about 2% by weight or about 1% by weight water. In certain embodiments of the present invention, an amphiphilic compound absorbs less than about 0.5% by weight water vapor and thus a pharmaceutical composition of the present invention may comprise less than about 0.5% by weight water.

An amphiphilic compound may have a hydrophilic-lipophilic balance (HLB) value of 12 to 20 or any range therein, such as, but not limited to, 15 to 20 or 18 to 20. In certain embodiments of the present invention, an amphiphilic compound comprises a HLB value of 19.

Exemplary amphiphilic compounds include, but are not limited to, fatty acid esters. One or more fatty acid ester(s) may be present in the pharmaceutical compositions of the present invention, such as 2, 3, 4, or more fatty acid esters. Exemplary fatty acid esters include, but are not limited to, $C_6$-$C_{22}$ alkyl and/or alkenyl fatty acid esters such as methyl laurate, ethyl laurate, ethyl myristate, ethyl palmitate, ethyl linoleate, propyl isobutylate, isopropyl laurate, isopropyl myristate, isopropyl palmitate, oleyl myristate, oleyl stearate, and oleyl oleate; ether-esters such as fatty acid esters of ethoxylated fatty alcohols; polyhydric alcohol esters such as ethylene glycol mono- and di-fatty acid esters, diethylene glycol mono- and di-fatty acid esters; polyethylene glycol (6-2000) fatty acid mono- and/or diesters such as PEG-6-laurate, PEG-6-stearate, PEG-8-dilaurate, PEG-8-distearate, etc.; polyethylene glycol glycerol fatty acid esters such as PEG-20-glyceryl laurate, PEG-20-glyceryl stearate, and PEG-20-glyceryl oleate; propylene glycol mono- and di-fatty acid esters; polypropylene glycol 2000 monooleate; polypropylene glycol 2000 monostearate; ethoxylated propylene glycol monostearate; glyceryl mono- and di-fatty acid esters; polyglycerol fatty acid esters such as polyglyceryl-10 laurate, etc.; ethoxylated glyceryl monostearate; 1,3-butylene glycol monostearate; 1,3-butylene glycol distearate; polyoxyethylene polyol fatty acid ester; sorbitan fatty acid esters including sorbitan trioleate and sorbitan monolaurate; polyethylene glycol sorbitan fatty acid esters such as PEG-6 sorbitan monooleate; polyoxyethylene sorbitan fatty acid esters including polyoxyethylene (20) sorbitan monolaurate; sucrose fatty acid esters such as saccharose monopalmitate and saccharose monostearate; wax esters such as beeswax, spermaceti, myristyl myristate, stearyl stearate and arachidyl behenate; polyethylene glycol alkyl ethers such as PEG-10 oleyl ether or PEG-9 cetyl ether; polyethylene glycol alkyl phenols such as PEG-10-100 nonyl phenol; polyoxyethylene-polyoxypropylene block copolymers such as poloxamer 188; sterol esters such as cholesterol fatty acid esters, and any combination thereof.

A fatty acid ester may comprise a polyethylene glycol (PEG) glyceride. The polyethylene glycol portion of a PEG glyceride may provide the hydrophilic property of an amphiphilic compound and may include, but is not limited to, PEG 5-1000 or any range therein, and any combination thereof. The glyceride portion of a PEG glyceride may provide the hydrophobic property of an amphiphilic compound and may include, but is not limited to, a natural and/or hydrogenated oil, such as but not limited to, castor oil, hydrogenated castor oil, vitamin A, vitamin D, vitamin E, vitamin K, a plant oil (e.g., corn oil, olive oil, peanut oil, palm kernel oil, apricot kernel oil, almond oil, etc.), and any combination thereof. Exemplary polyethylene glycol (PEG) glycerides include, but are not limited to, PEG-20 castor oil, PEG-20 hydrogenated castor oil, PEG-20 corn glycerides, PEG-20 almond glycerides; PEG-23 trioleate, PEG-40 palm kernel oil, PEG-8 caprylic/capric glycerides, PEG-6 caprylic/capric glycerides, lauroyl macrogol-32 glyceride, stearoyl macrogol glyceride, tocopheryl PEG-1000 succinate, and any combination thereof. In some embodiments of the present invention a fatty acid ester comprises a PEG 5-30 (i.e., PEG 5, 6, 7, 8, 9, 10, etc.) and a caprylic/capric glyceride. In particular embodiments of the present invention, a pharmaceutical composition comprises a PEG-5-caprylic/capric glyceride, a PEG-6-caprylic/capric glyceride, a PEG-7-caprylic/capric glyceride, and/or a PEG-8-caprylic/capric glyceride. In certain embodiments of the present invention, a pharmaceutical composition comprises one or more fatty acid esters such as, but not limited to, those commercially available from Sasol of Hamburg, Germany under the trademark SOFTIGEN®.

An amphiphilic compound may be present in a pharmaceutical composition of the present invention at a concentration from about 1% to about 30% by weight or any range therein, such as, but not limited to, from about 2% to about 20% by weight or about 5% to about 15% by weight. In certain embodiments of the present invention, an amphiphilic compound is present in a pharmaceutical composition of the present invention at a concentration of about 10% by weight.

A pharmaceutical composition of the present invention may further comprise one or more excipients. Excipients for use in pharmaceutical compositions are well-known in the art and examples may be found in the Handbook of Pharmaceutical Excipients (Rowe, R. C. et al., APhA Publications; 5th ed., 2005). Classes of excipients may include, but are not limited to, an emollient, a humectant, a cosolvent, a pH modifier, a water repelling agent, an anti-foaming agent, a surfactant, a solubilizer, a wetting agent, a penetration enhancer, an antioxidant, and/or a solvent. The excipients may be present in a pharmaceutical composition of the present invention at any suitable concentration.

In particular embodiments of the present invention, a pharmaceutical composition may further comprise a cosolvent. A cosolvent may be present in a pharmaceutical composition of the present invention at a concentration from about 1% to about 30% by weight or any range therein, such as, but not limited to, from about 2% to about 20% by weight or about 5% to about 15% by weight. In certain embodiments of the present invention, a cosolvent is present in a pharmaceutical composition of the present invention at a concentration from about 10% to about 15% by weight.

Exemplary cosolvents include, but are not limited to, a fatty acid ester, propylene glycol, glycerol, polyethylene glycol. In some embodiments of the present invention, a cosolvent may comprise a neutral oil. In certain embodiments of the present invention, a cosolvent comprises a caprylic and/or capric triglyceride such as, but not limited to, those commercially available from Sasol of Hamburg, Germany under the trademark MIGLYOL®.

The pharmaceutical compositions of the present invention may comprise a humectant. Any suitable humectant or combination of humectants may be used. A humectant may be present in a pharmaceutical composition of the present invention at a concentration from about 1% to about 25% by weight or any range therein, such as, but not limited to, from about 2% to about 20% by weight or about 5% to about 15% by weight. In certain embodiments of the present invention, a humectant is present in a pharmaceutical composition of the present invention at a concentration from about 10% to about 15% by weight.

Exemplary humectants include, but are not limited to, glycols, such as a polyhydric alcohol, diethylene glycol monoethyl ether and methoxypolyethyleneglycol; glycerols such as propylene glycol, glycerol, isopropanol, ethanol, ethylene glycol, polyethylene glycol, ethoxydiglycol or mixtures thereof; sugar polyols, such as sorbitol, xylitol and maltitol; polyols such as polydextroses; dimethyl isosorbide; quillaia; urea; and any combination thereof. In particular embodiments of the present invention, a humectant comprises an alkylene glycol, such as hexylene glycol, butylene glycol, pentylene glycol, and any combination thereof.

A pharmaceutical composition of the present invention may comprise an active pharmaceutical ingredient (API). The API may be present in a pharmaceutical composition of the present invention at any suitable concentration. In particular embodiments of the present invention, the API comprises a moisture activated active pharmaceutical ingredient, such as, but not limited to, a nitric oxide-releasing compound and/or a water soluble API. In some embodiments of the present invention, a pharmaceutical composition of the present invention may provide a controlled and/or sustained release of the API by controlling the amount of moisture absorbed by the pharmaceutical composition. In particular embodiments of the present invention, a moisture activated API is present in the composition at a concentration from about 0.1% to about 70% by weight or any range therein, such as, but not limited to, from about 1% to about 50% by weight or from about 2% to about 30% by weight.

In order to avoid a gritty feeling in a pharmaceutical composition of the present invention, the maximum particle size for a the API may be less than about 100 μm and, in some embodiments, less than about 20 μm, and in further embodiments, less than about 10 μm.

Any suitable active pharmaceutical ingredient (API) or combinations of APIs may be included in the compositions according to embodiments of the invention. Examples of APIs include, but are not limited to, antimicrobial agents, anti-acne agents, anti-inflammatory agents, analgesic agents, anesthetic agents, antihistamine agents, antiseptic agents, immunosuppressants, antihemorrhagic agents, vasodilators, wound healing agents, anti-biofilm agents and mixtures thereof.

Examples of antimicrobial agents include, but are not limited to, penicillins and related drugs, carbapenems, cephalosporins and related drugs, erythromycin, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomysin, tetracyclines, vanomycin, teicoplanin, streptogramins, anti-folate agents including sulfonamides, trimethoprim and its combinations and pyrimethamine, synthetic anti-bacterials including nitrofurans, methenamine mandelate and methenamine hippurate, nitroimidazoles, quinolones, fluoroquinolones, isoniazid, ethambutol, pyrazinamide, para-aminosalicylic acid (PAS), cycloserine, capreomycin, ethionamide, prothionamide, thiacetazone, viomycin, eveminomycin, glycopeptide, glyclyclycline, ketolides, oxazolidinone; imipenen, amikacin, netilmicin, fosfomycin, gentamycin, ceftriaxone, Ziracin, Linezolid, Synercid, Aztreonam, and Metronidazole, Epiroprim, Sanfetrinem sodium, Biapenem, Dynemicin, Cefluprenam, Cefoselis, Sanfetrinem celexetil, Cefpirome, Mersacidin, Rifalazil, Kosan, Lenapenem, Veneprim, Sulopenem, ritipenam acoxyl, Cyclothialidine, micacocidin A, carumonam, Cefozopran and Cefetamet pivoxil.

Examples of topical anti-acne agents include, but are not limited to, adapalene, azelaic acid, benzoyl peroxide, clindamycin and clindamycin phosphate, doxycycline, erythromycin, keratolytics such as salicylic acid and retinoic acid (Retin-A"), norgestimate, organic peroxides, retinoids such as isotretinoin and tretinoin, sulfacetamide sodium, and tazarotene. Particular anti-acne agents include adapalene, azelaic acid, benzoyl peroxide, clindamycin (e.g., clindamycin phosphate), doxycycline (e.g., doxycycline monohydrate), erythromycin, isotretinoin, norgestimate, sulfacetamide sodium, tazarotene, etretinate and acetretin.

Examples of antihistamine agents include, but are not limited to, diphenhydramine hydrochloride, diphenhydramine salicylate, diphenhydramine, chlorpheniramine hydrochloride, chlorpheniramine maleate isothipendyl hydrochloride, tripelennamine hydrochloride, promethazine hydrochloride, methdilazine hydrochloride, and the like. Examples of local anesthetic agents include dibucaine hydrochloride, dibucaine, lidocaine hydrochloride, lidocaine, benzocaine, p-buthylaminobenzoic acid 2-(die-ethylamino) ethyl ester hydrochloride, procaine hydrochloride, tetracaine, tetracaine hydrochloride, chloroprocaine hydrochloride, oxyprocaine hydrochloride, mepivacaine, cocaine hydrochloride, piperocaine hydrochloride, dyclonine and dyclonine hydrochloride.

Examples of antiseptic agents include, but are not limited to, alcohols, quaternary ammonium compounds, boric acid, chlorhexidine and chlorhexidine derivatives, iodine, phenols, terpenes, bactericides, disinfectants including thimerosal, phenol, thymol, benzalkonium chloride, benzethonium chloride, chlorhexidine, povidone iode, cetylpyridinium chloride, eugenol and trimethylammonium bromide.

Examples of anti-inflammatory agents include, but are not limited to, nonsteroidal anti-inflammatory agents (NSAIDs); propionic acid derivatives such as ibuprofen and naproxen; acetic acid derivatives such as indomethacin; enolic acid derivatives such as meloxicam, acetaminophen; methyl salicylate; monoglycol salicylate; aspirin; mefenamic acid; flufenamic acid; indomethacin; diclofenac; alclofenac; diclofenac sodium; ibuprofen; ketoprofen; naproxen; pranoprofen; fenoprofen; sulindac; fenclofenac; clidanac; flurbiprofen; fentiazac; bufexamac; piroxicam; phenylbutazone; oxyphenbutazone; clofezone; pentazocine; mepirizole; tiaramide hydrochloride; steroids such as clobetasol propionate, bethamethasone dipropionate, halbetasol proprionate, diflorasone diacetate, fluocinonide, halcinonide, amcinonide, desoximetasone, triamcinolone acetonide, mometasone furoate, fluticasone proprionate, betamethasone diproprionate, triamcinolone acetonide, fluticasone propionate, desonide, fluocinolone acetonide, hydrocortisone vlaerate, prednicarbate, triamcinolone acetonide, fluocinolone acetonide, hydrocortisone and others known in the art, predonisolone, dexamethasone, fluocinolone acetonide, hydrocortisone acetate, predonisolone acetate, methylpredonisolone, dexamethasone acetate, betamethasone, betamethasone valerate, flumetasone, fluorometholone, beclomethasone diproprionate, fluocinonide, topical corticosteroids, and may be one of the lower potency corticosteroids such as hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17,21-diesters (e. g., hydrocortisone-17,21-diacetate, hydrocortisone-17-acetate-21-butyrate, hydrocortisone-17,21-dibutyrate, etc.), alclometasone, dexamethasone, flumethasone, prednisolone, or methylprednisolone, or may be a higher potency corticosteroid such as clobetasol propionate, betamethasone benzoate, betamethasone dipropionate, diflorasone diacetate, fluocinonide, mometasone furoate, triamcinolone acetonide.

Examples of analgesic agents include, but are not limited to, alfentanil, benzocaine, buprenorphine, butorphanol, butamben, capsaicin, clonidine, codeine, dibucaine, enkephalin, fentanyl, hydrocodone, hydromorphone, indomethacin, lidocaine, levorphanol, meperidine, methadone, morphine, nicomorphine, opium, oxybuprocaine, oxycodone, oxymorphone, pentazocine, pramoxine, proparacaine, propoxyphene, proxymetacaine, sufentanil, tetracaine and tramadol.

Examples of anesthetic agents include, but are not limited to, alcohols such as phenol; benzyl benzoate; calamine; chloroxylenol; dyclonine; ketamine; menthol; pramoxine; resorcinol; troclosan; procaine drugs such as benzocaine, bupivacaine, chloroprocaine; cinchocaine; cocaine; dexivacaine; diamocaine; dibucaine; etidocaine; hexylcaine; levobupivacaine; lidocaine; mepivacaine; oxethazaine; prilocaine; procaine; proparacaine; propoxycaine; pyrrocaine; risocaine; rodocaine; ropivacaine; tetracaine; and derivatives, such as pharmaceutically acceptable salts and esters including bupivacaine HCl, chloroprocaine HCl, diamocaine cyclamate, dibucaine HCl, dyclonine HCl, etidocaine HCl, levobupivacaine HCl, lidocaine HCl, mepivacaine HCl, pramoxine HCl, prilocaine HCl, procaine HCl, proparacaine HCl, propoxycaine HCl, ropivacaine HCl, and tetracaine HCl.

Examples of antihemorrhagic agents include, but are not limited to, thrombin, phytonadione, protamine sulfate, aminocaproic acid, tranexamic acid, carbazochrome, carbaxochrome sodium sulfanate, rutin and hesperidin.

In some embodiments of the present invention, an active pharmaceutical ingredient (API) comprises, consists essentially of, or consists of a compound that releases nitric oxide (NO). Any suitable NO-releasing compound may be used in a pharmaceutical composition of the present invention. In some embodiments of the present invention, the NO-releasing compound comprises a small molecule compound that includes an NO donor group. "Small molecule compound" as used herein refers to a compound having a molecular weight of less than 500 daltons, and includes organic and/or inorganic small molecules. In some embodiments of the present invention, the NO-releasing compound comprises a macromolecule that includes an NO donor group. A "macromolecule" as used herein refers to a compound that has a molecular weight of 500 daltons or greater. Any suitable macromolecule may be used, including crosslinked or non-crosslinked polymers, dendrimers, metallic compounds, organometallic compounds, inorganic-based compounds, and other macromolecular scaffolds. In some embodiments, the macromolecule has a nominal diameter ranging from about 0.1 nm to about 100 μm and may comprise the aggregation of two or more macromolecules, whereby the macromolecular structure is further modified with a NO donor group.

In certain embodiments of the present invention, the NO donor of a NO-releasing compound releases nitric oxide upon exposure to an external condition, such as light, heat, water, acid, base, and/or the like. For example, in some embodiments of the present invention, the NO-releasing compound comprises a diazeniumdiolate functional group as an NO donor. The diazeniumdiolate functional group may produce nitric oxide under certain conditions, such as upon exposure to water. As another example, in some embodiments of the present invention, a NO-releasing compound may comprise, but is not limited to, a nitrosothiol functional group as the NO donor. The NO donor may produce nitric oxide under certain conditions, such as upon exposure to light. Examples of other NO donor groups include, but are not limited to, nitrosamine, hydroxyl nitrosamine, hydroxyl amine and hydroxyurea. Any suitable combination of NO donors and/or NO-releasing compounds may be used in a pharmaceutical composition of the present invention. Additionally, the NO donor may be incorporated into and/or onto a small molecule and/or macromolecule through covalent and/or non-covalent interactions.

In some embodiments of the present invention, the NO-releasing compounds may be in the form of NO-releasing particles, such as those described in U.S. Publication No. 2009/0214618, the disclosure of which is incorporated by reference herein in its entirety. Such particles may be prepared by methods described therein.

The NO-releasing compound may release nitric oxide by any suitable mechanism, including via reaction with water and/or thermal degradation. Examples of NO-releasing functional groups that may be included in the NO-releasing compound include, but are not limited to, diazeniumdiolate, nitrosamine, hydroxyl nitrosamine, nitrosothiol, hydroxyl amine, hydroxyurea, and metal nitrosyl complexes. Other NO-releasing functional groups that are capable of releasing nitric oxide in a therapeutic manner, such as acidified nitrite, may also be utilized.

The NO-releasing compound may be a small molecule compound, an oligomer and/or a polymer and may be in any suitable physical form, such as, but not limited to, a particle, coating, film, liquid, solution and the like. In some embodiments, the nitric oxide-releasing compound comprises diazeniumdiolate-functionalized polysiloxane macromolecules as described above. Other non-limiting examples of NO-releasing compounds include NO-releasing zeolites as described in United States Patent Publication Nos. 2006/0269620 or 2010/0331968; NO-releasing metal organic frameworks (MOFs) as described in United States Patent Application Publication Nos. 2010/0239512 or 2011/0052650; NO-releasing multi-donor compounds as described in U.S. Provisional Patent Application Ser. No. 61/526,918 entitled "Tunable Nitric Oxide-Releasing Macromolecules Having Multiple Nitric Oxide Donor Structures"; NO-releasing dendrimers or metal structures as described in U.S. Publication No. 2009/0214618; nitric oxide releasing coatings as described in U.S. Publication No. 2011/0086234; and compounds as described in U.S. Publication No. 2010/0098733. The disclosures of each of the references in this paragraph are incorporated herein by reference in their entirety. Additionally, NO-releasing macromolecules may be fabricated as described in International Application No. PCT/US2012/022048 entitled "Temperature Controlled Sol-Gel Co-Condensation" filed Jan. 20, 2012, the disclosure of which is incorporated herein by reference in its entirety.

As an example, in some embodiments of the invention, the NO-releasing particles include NO-loaded precipitated silica. The NO-loaded precipitated silica may be formed from nitric oxide donor modified silane monomers into a co-condensed siloxane network. In one embodiment of the invention, the nitric oxide donor is an N-diazeniumdiolate.

In some embodiments, the nitric oxide donor may be formed from an aminoalkoxysilane by a pre-charging method, and the co-condensed siloxane network may be synthesized from the condensation of a silane mixture that includes an alkoxysilane and the aminoalkoxysilane to form a nitric oxide donor modified co-condensed siloxane network. As used herein, the "pre-charging method" means that aminoalkoxysilane is "pretreated" or "precharged" with nitric oxide prior to the co-condensation with alkoxysilane. In some embodiments, the precharging nitric oxide may be accomplished by chemical methods. In another embodiment, the "pre-charging" method may be used to create co-condensed siloxane networks and materials more densely functionalized with NO-donors.

The co-condensed siloxane network may be silica particles with a uniform size, a collection of silica particles with a variety of size, amorphous silica, a fumed silica, a nanocrystalline silica, ceramic silica, colloidal silica, a silica coating, a silica film, organically modified silica, mesoporous silica, silica gel, bioactive glass, or any suitable form or state of silica.

In some embodiments, the alkoxysilane is a tetraalkoxysilane having the formula $Si(OR)_4$, wherein R is an alkyl group. The R groups may be the same or different. In some embodiments the tetraalkoxysilane is selected as tetramethyl orthosilicate (TMOS) or tetraethyl orthosilicate (TEOS). In some embodiments, the aminoalkoxysilane has the formula: R''—(NH—R')n-Si(OR)3, wherein R is alkyl, R' is alkylene, branched alkylene, or aralkylene, n is 1 or 2, and R'' is selected from the group consisting of alkyl, cycloalkyl, aryl, and alkylamine.

In some embodiments, the aminoalkoxysilane may be selected from N-(6-aminohexyl)aminopropyltrimethoxysilane (AHAP3); N-(2-aminoethyl)-3-aminopropyltrimethoxysilane (AEAP3); (3-trimethoxysilylpropyl)di-ethylenetriamine (DET3); (aminoethylaminomethyl) phenethyltrimethoxysilane (AEMP3); [3-(methylamino) propyl]trimethoxysilane (MAP3); N-butylamino-propyltrimethoxysilane(n-BAP3); t-butylamino-propyltrimethoxysilane(t-BAP3); N-ethylaminoisobutyltrimethoxysilane(EAiB3); N-phenylamino-propyltrimethoxysilane (PAP3); and N-cyclohexylaminopropyltrimethoxysilane (cHAP3).

In some embodiments, the aminoalkoxysilane has the formula: NH [R'—Si(OR)3]2, wherein R is alkyl and R' is alkylene. In some embodiments, the aminoalkoxysilane may be selected from bis(3-triethoxysilylpropyl)amine, bis-[3-(trimethoxysilyl)propyl]amine and bis-[(3-trimethoxysilyl) propyl]ethylenediamine.

In some embodiments, as described herein above, the aminoalkoxysilane is precharged for NO-release and the amino group is substituted by a diazeniumdiolate. Therefore, in some embodiments, the aminoalkoxysilane has the formula: R''—N(NONO—X+)-R'—Si(OR)3, wherein R is alkyl, R' is alkylene or aralkylene, R'' is alkyl or alkylamine, and X+ is a cation selected from the group consisting of Na+, K+ and Li+.

The composition of the siloxane network, (e.g., amount or the chemical composition of the aminoalkoxysilane) and the nitric oxide charging conditions (e.g., the solvent and base) may be varied to optimize the amount and duration of nitric oxide release. Thus, in some embodiments, the composition of the silica particles may be modified to regulate the half-life of NO release from silica particles.

In another embodiment, the amino group of aminoalkoxysilane is substituted with a diazeniumdiolate, and the aminoalkoxysilane having a formula of R"—N(NONO—X+)-R'—Si(OR)3, wherein: R is alkyl, R' is alkylene or aralkylene, R" is alkyl or alkylamine, and X+ is a cation selected from the group consisting of Na+ and K+.

In some embodiments of the invention, the particle size of the NO-releasing particles is in a range of 20 nm and 10 μm. The particle size may be tailored to minimize or prevent toxicity and penetration through the epidermis (or compromised dermis) and into the blood vessels. In particular embodiments, the particle size is distributed around a mean particle size of less than about 10 μm to allow the particle to enter a follicle. In further embodiments, the particle size is distributed around a mean particle size of less than about 8 μm. In other embodiments, the particle size is distributed around a mean particle size of greater than about 10 μm to prevent the particle from entering the follicle.

In still further embodiments, a mixture of particles with mean particle sizes distributed around two or more mean particle sizes may be provided. For example, a mixture of particles having a particle size distributed around a mean particle size of less than about 10 μm to allow the particle to enter a follicle may be mixed with particles having a particle size distributed around a mean particle size of greater than about 10 μm to prevent the particle from entering the follicle. The particles may have the same nitric oxide release profiles or different nitric oxide release profiles. For example, the smaller particles may have a release profile tailored to enhance their ability to moderate sebum production and/or abnormal keratinization and the larger particles may have a release profile tailored to enhance their ability to kill bacteria, promote wound healing, reduce scarring or other desirable therapeutic effect provided by nitric oxide. Other combinations and multiple combinations could also be provided.

A pharmaceutical composition of the present invention may be prepared by any suitable method. However, in some embodiments, a composition of the present invention may be manufactured by a method described in U.S. Provisional Patent Application Ser. Nos. 61/504,626 and 61/610,179, both entitled "Methods of Manufacturing Topical Compositions and Apparatus For Same," filed Jul. 5, 2011 and Mar. 13, 2012, respectively, which are hereby incorporated by reference herein in their entirety.

In certain embodiments of the present invention, a method of preparing a pharmaceutical composition of the present invention comprises homogenizing a first excipient composition comprising a hydrophobic base, an amphiphilic compound, and optionally a cosolvent. A mechanical overhead agitation device may be used to mix a first excipient composition until the desired uniformity and/or consistency is achieved. The homogenization speed and/or rate may be constant, varied, increased, and/or decreased to achieve the desired uniformity and/or consistency. In particular embodiments of the present invention, a first excipient composition of the present invention is mixed until the composition is visually uniform. In some embodiments of the present invention, the method further comprises separately homogenizing a second excipient composition comprising a hydrophobic base, an active pharmaceutical ingredient, and optionally a humectant. The first excipient composition and second excipient composition may then be combined to form a pharmaceutical composition of the present invention.

FIG. 1 is a flowchart of operations for an exemplary embodiment of the present invention. As seen in FIG. 1, operations begin by dispensing raw materials for use in the process (block 100). Then the temperature of the mixing vessels is set (block 110). A hydrophobic base and amphiphilic compound are added to a vessel (block 120) optionally with a cosolvent (block 125) to form a first excipient composition. The homogenization parameters (e.g., the homogenization rate, time, etc.) are then set and homogenization of the first excipient composition is begun (block 130). In particular embodiments of the present invention, after adding the components of the first excipient composition, the homogenization speed is increased compared to the initial speed and maintained until a visually uniform composition is obtained. In a separate vessel, a hydrophobic base and an active pharmaceutical ingredient (API), such as, but not limited to, a moisture activated API, are combined (block 140) optionally with a humectant (block 145) to form a second excipient composition. The homogenization parameters (e.g., the homogenization rate, time, etc.) are then set and homogenization of the second excipient composition is begun (block 150). Next, the first and second excipient compositions are combined and homogenized until the desired uniformity is obtained (block 160).

Any suitable homogenization mechanism may be used. Examples of homogenization devices include mechanical overhead agitation such as propeller, anchor, pitch blade, rotor-stator, rotating blades, ultrasonic devices, in-line and high pressure homogenizers. Any of these methods may be used, and multiple methods may be used in combination in some embodiments. Homogenization of the premix compositions may provide a final topical composition that has desirable API stability and blend homogeneity. In some embodiments of the present invention, an in-line homogenizer may be used. In particular embodiments of the present invention, a homogenization method and/or device may be used that maintains an active pharmaceutical ingredient (e.g., a moisture activated active pharmaceutical ingredient) below a temperature at which the active pharmaceutical ingredient could degrade. An active pharmaceutical ingredient may degrade at a particular temperature if maintained at that temperature for a specific duration of time. Accordingly, in some embodiments of the present invention, the duration of time an active pharmaceutical ingredient is maintained at a particular temperature, is below the time period at which the active ingredient could degrade at that temperature. In certain embodiments of the present invention, for the entire homogenization process, the active pharmaceutical ingredient is kept at a temperature that does not exceed the temperature at which the active pharmaceutical ingredient could degrade.

In some embodiments of the present invention, homogenization is performed at a temperature in a range from about −15° C. to about 30° C. or any range therein. In particular embodiments of the present invention, the homogenization is performed at room temperature. In some embodiments of the present invention, homogenization is performed in a dry, inert atmosphere, such that water and oxygen are substantially absent from the homogenization vessel.

A pharmaceutical composition of the present invention may be used to treat the skin of a subject by topically administering the pharmaceutical composition. Accordingly, another aspect of the present invention comprises a method of treating the skin of a subject, the method comprising topically administering a pharmaceutical composition of the present invention to the skin of a subject. In some embodiments of the present invention, when a moisture activated active pharmaceutical ingredient is present in a pharmaceutical composition of the present invention, the method may further comprise contacting moisture (e.g., water) to the composition and/or application site before, after, and/or during the step of topically administering the composition. In some embodiments of the present invention, moisture, such as, but not limited to water and/or a bodily fluid, is already present at the application site prior to administration of a pharmaceutical composition of the present invention.

Any portion of a subject's skin may be treated, including, but not limited to, a mucous membrane (including a body cavity), nail, and/or scalp of the subject. However, in some embodiments of the present invention, one or more of the subject's appendages are treated by a method described herein. Furthermore, in some embodiments of the present invention, the subject's trunk is treated by a method described herein.

The present invention finds use in both veterinary and medical applications. Subjects suitable to be treated with a method embodiment of the invention include, but are not limited to, avian and mammalian subjects. Mammals of the present invention include, but are not limited to, canines, felines, bovines, caprines, equines, ovines, porcines, rodents (e.g. rats and mice), lagomorphs, primates (e.g., simians and humans), non-human primates (e.g., monkeys, baboons, chimpanzees, gorillas), and the like, and mammals in utero. Any mammalian subject in need of being treated according to the present invention is suitable. Human subjects of both genders and at any stage of development (i.e., neonate, infant, juvenile, adolescent, adult) may be treated according to the present invention. In some embodiments of the present invention, the subject is a mammal and in certain embodiments the subject is a human. Human subjects include both males and females of all ages including fetal, neonatal, infant, juvenile, adolescent, adult, and geriatric subjects as well as pregnant subjects. In particular embodiments of the present invention, the subject is a human adolescent and/or adult.

Illustrative avians according to the present invention include chickens, ducks, turkeys, geese, quail, pheasant, ratites (e.g., ostrich) and domesticated birds (e.g., parrots and canaries), and birds in ovo.

The methods of the present invention may also be carried out on animal subjects, particularly mammalian subjects such as mice, rats, dogs, cats, livestock and horses for veterinary purposes, and/or for drug screening and drug development purposes.

In particular embodiments of the present invention, the subject is "in need of" the methods of the present invention, e.g., the subject has been diagnosed with, is at risk for, and/or is believed to have a disease or disorder that may be treated using the methods of the present invention. In some embodiments of the present invention, the subject has a skin disorder, such as, but not limited to, acne, atopic dermatitis, and/or psoriasis. In other embodiments of the present invention, the subject has a wound, such as, but not limited to, a bed sore, a burn, and/or a diabetic foot ulcer. In some embodiments of the present invention, the subject has an inflammatory skin condition or disorder.

"Treat," "treating" or "treatment of" (and grammatical variations thereof) as used herein refer to any type of treatment that imparts a benefit to a subject and may mean that the severity of the subject's condition is reduced, at least partially improved or ameliorated and/or that some alleviation, mitigation or decrease in at least one clinical symptom is achieved and/or there is a delay in the progression of the disease or disorder. In particular embodiments of the present invention, the severity of the skin disorder is reduced in a subject compared to the severity of the skin disorder in the absence of the methods of the present invention. In other embodiments of the present invention, the methods of the present invention improve wound healing and/or prevent against infection.

The present invention is explained in greater detail in the following non-limiting Examples.

EXAMPLES

Example 1

Tables 1 and 2 set forth various pharmaceutical compositions prepared according to embodiments of the present invention.

TABLE 1

Pharmaceutical compositions comprising formulation 1.

| Ingredient | % w/w | | | |
|---|---|---|---|---|
| | 2% | 4% | 8% | 16% |
| Versagel P200 Butylene/Ethylene/Styrene copolymer in Petrolatum | 50.0 | 50.0 | 50.0 | 45.0 |
| Hexylene glycol | 12.0 | 12.0 | 12.0 | 12.0 |
| Nitricil ™ | 2.0 | 4.0 | 8.0 | 16.0 |
| Softigen 767 (PEG-6-Caprylic/capric glyceride) Caprylocaproyl polyoxylglyceride, NF | 10.0 | 10.0 | 10.0 | 10.0 |
| Light Mineral Oil, NF | 10.5 | 9.5 | 7.5 | 6.0 |
| Mineral Oil, USP | 10.5 | 9.5 | 7.5 | 6.0 |
| Miglyol 840 Propylene glycol dicaprylate/dicaprate, NF | 5.0 | 5.0 | 5.0 | 5.0 |
| Total | 100.0 | 100.0 | 100.0 | 100.0 |

TABLE 2

Pharmaceutical compositions comprising formulation 2.

| Ingredient | % w/w | | | |
|---|---|---|---|---|
| | 2% | 4% | 12% | 20% |
| Crodabase SQ Mineral oil and Polyethylene | 50.0 | 50.0 | 47.0 | 40.0 |
| Nitricil ™ | 2.0 | 4.0 | 12.0 | 20.0 |
| Hexylene glycol | 12.0 | 12.0 | 12.0 | 12.0 |
| Miglyol 812 Medium Chain Triglycerides, NF | 12.0 | 12.0 | 12.0 | 12.0 |
| Softigen 767 (PEG-6-Caprylic/capric glyceride) Caprylocaproyl polyoxylglyceride, NF | 10.0 | 10.0 | 10.0 | 10.0 |
| Light Mineral Oil, NF | 14.0 | 12.0 | 7.0 | 6.0 |
| Total | 100.0 | 100.0 | 100.0 | 100.0 |

Example 2

Ointment formulations with 2% Nitricil™ comprising MAP3 as described in U.S. Publication No. 2009/0214618 and in International Application No. PCT/US2012/022048 entitled "Temperature Controlled Sol-Gel Co-Condensation" filed Jan. 20, 2012 were prepared. Tables 3-6 show the formulations of the ointments and gels produced. Ointment formulations in Tables 4 and 5 were prepared as described herein. A version of the ointment in Table 4 was also prepared without Nitricil™ active ingredient, with the active ingredient replaced with Mineral Oil and Light Mineral Oil. The ointment described in Table 3 was prepared as described in U.S. patent application Ser. No. 12/860,457. The topical gel in Table 6 was produced as described in U.S. Provisional Patent Application Ser. No. 61/504,628.

TABLE 3

Ointment comprising formulation 11-15-12.

| Ingredient | % w/w |
|---|---|
| Mineral Oil, USP | 73.0 |
| Captex 300 | 10.0 |
| Miglyol 840 | 10.0 |
| Cab-o-sil M5P | 5.0 |
| Nitricil ™ | 2.0 |
| Total | 100.0 |

TABLE 4

Ointment comprising formulation T0-005.

| Ingredient | % w/w |
|---|---|
| Versagel P200 | 50.0 |
| Hexylene glycol | 12.0 |
| Light Mineral Oil, NF | 10.5 |
| Mineral Oil, USP | 10.5 |
| Softigen 767 | 10.0 |
| Miglyol 840 | 5.0 |
| Nitricil ™ | 2.0 |
| Total | 100.0 |

TABLE 5

Ointment comprising formulation T0-006.

| Ingredient | % w/w |
|---|---|
| Glycerol, anhydrous | 76.0 |
| Hexylene glycol | 20.0 |
| Nitricil ™ | 2.0 |
| Polysorbate 80 | 1.0 |
| Sepineo P600 | 1.0 |
| Total | 100.0 |

TABLE 6

Alcohol Gel.

| Ingredient | % w/w |
|---|---|
| Ethyl alcohol, anhydrous, 200 proof | 83.5 |
| Hexylene glycol | 10.0 |
| Cyclomethicone, NF | 2.5 |
| Hydroxypropyl cellulose, NF | 2.0 |
| Nitricil ™ | 2.0 |
| Total | 100.0 |

Figure 2:
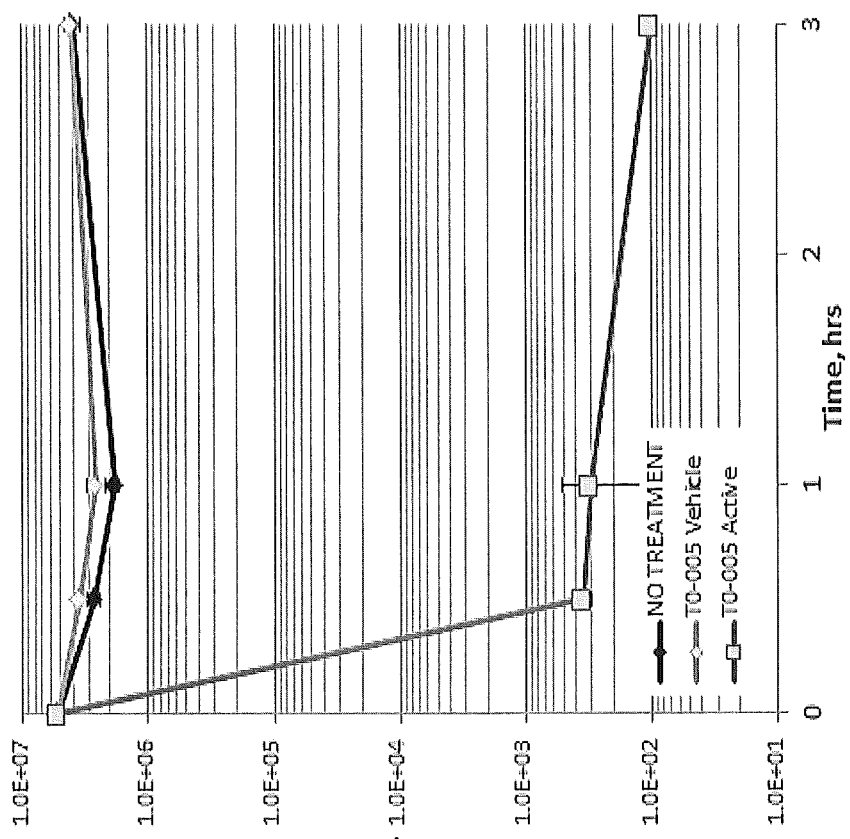
FIG. 2 shows a graph of time kill of *Pseudomonas aeruginosa* for ointments with 2% Nitricil™ and a topical gel with 2% Nitricil™ according to some embodiments of the present inventive concept.
Figure 3:
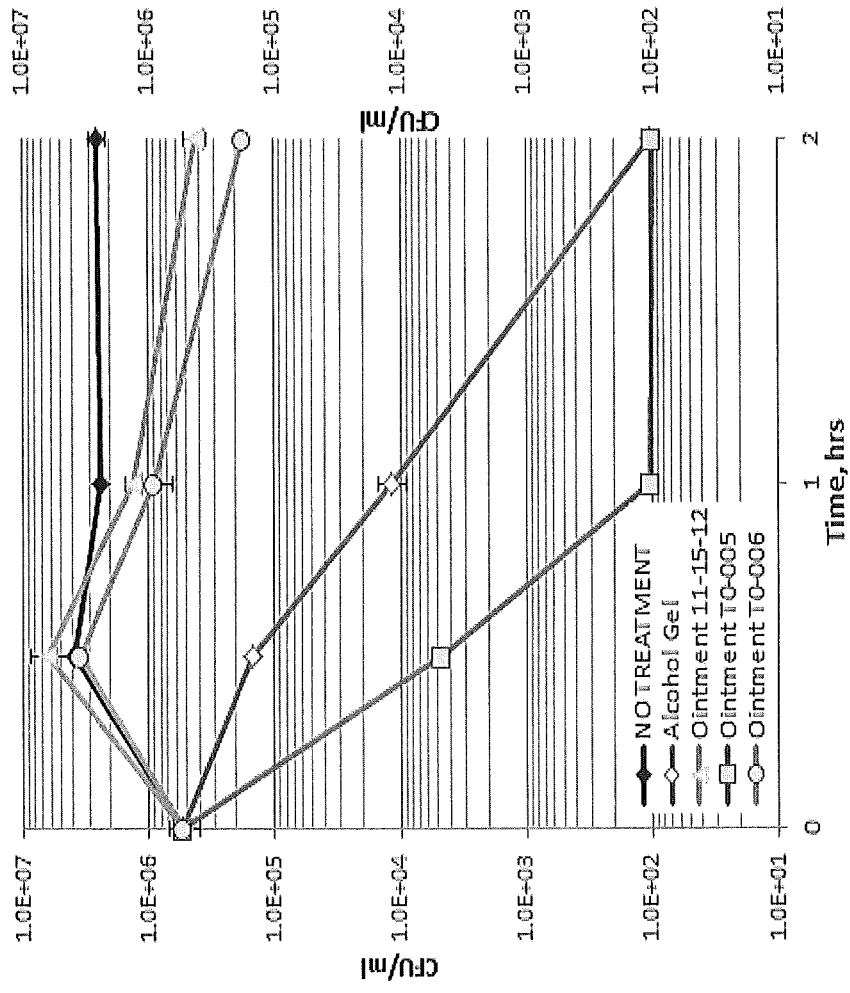
FIG. 3 shows a graph of time kill of *Pseudomonas aeruginosa* for an ointment with and without 2% Nitricil™ according to some embodiments of the present inventive concept.

The efficacies of the ointment formulations in Tables 4 and 5 were compared to an alcohol gel formulation (known to be bactericidal against *Pseudomonas aeruginosa*) shown in Table 6 and an earlier ointment formulation shown in Table 3. All formulations contained 2% Nitricil™ as described above and were tested at a dilution of 50 mg/ml in PBS for testing (equivalent to an Nitricil™ concentration of 1 mg/ml). FIG. 2 shows the results of the testing. Ointment formulation T0-005 was bactericidal against *P. aeruginosa* within one hour. FIG. 3 compares the time kill of the T0-005 formulation with and without Nitricil™. The T0-005 vehicle formulation exhibited no antibacterial activity (FIG. 3, bottom).

Example 3

Nitricil™ was produced as described in Example 2. A formulation as described in Table 7 was prepared as described herein.

TABLE 7

Ointment comprising formulation T0-2.

| Ingredient | % w/w |
|---|---|
| Crodabase SQ | 53.5 |
| Hexylene glycol | 12.0 |
| Miglyol 812 | 12.0 |
| Light Mineral Oil, NF | 10.5 |
| Softigen 767 | 10.0 |
| Nitricil ™ | 2.0 |
| Total | 100.0 |

A vehicle version of the T0-2 formulation was prepared by replacing Nitricil™ with Light Mineral Oil.

Figure 4:
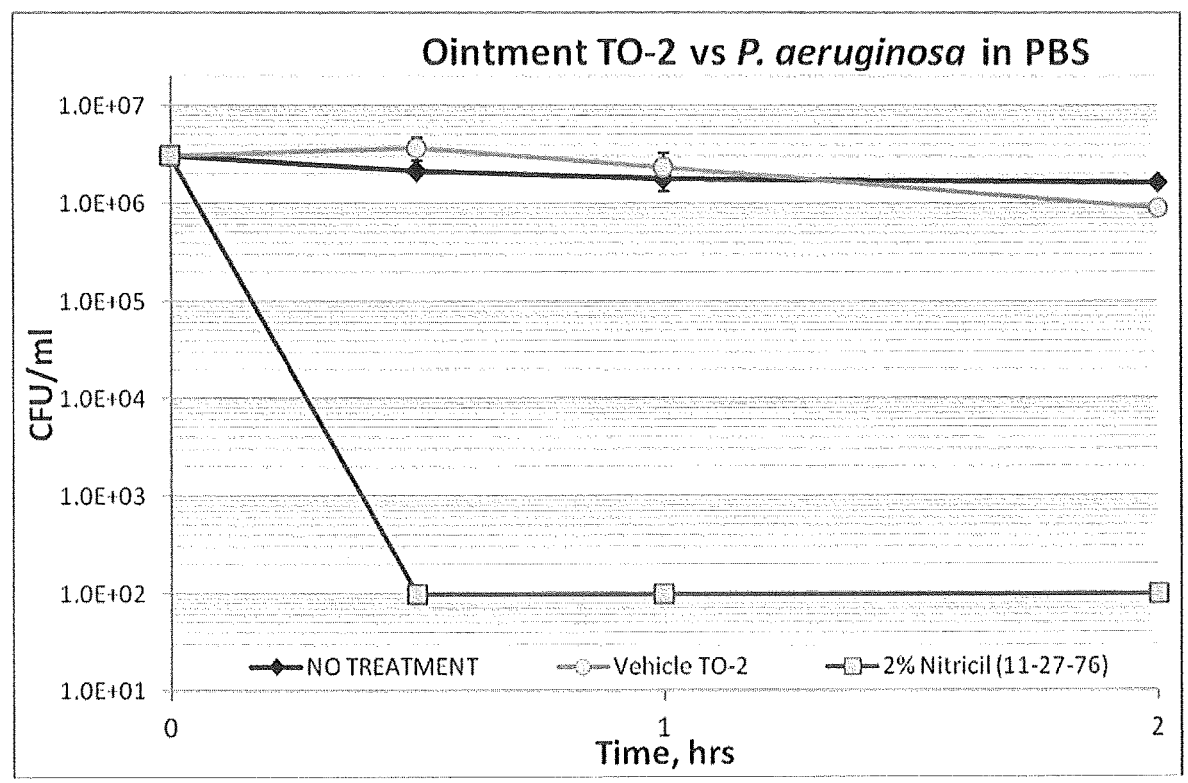
FIG. 4 shows a graph of time kill of *Pseudomonas aeruginosa* for an ointment with and without 2% Nitricil™ according to some embodiments of the present inventive concept.

All formulations contained 2% Nitricil™ as described above and were tested at a dilution of 50 mg/ml in PBS for testing (equivalent to an Nitricil™ concentration of 1 mg/ml) for time kill of *P. aeruginosa*. FIG. 4 shows the results of the testing. Ointment formulation T0-2 was bactericidal against *P. aeruginosa* within one hour whereas the vehicle was not.

Example 4

The efficacy of topical ointments according to the present inventive concept in reducing *Pseudomonas aeruginosa* in wounds was evaluated in a porcine animal model. Ointments were prepared as described wherein with regard to the 2% and 4% formulations as set forth in Table 1. Ointment without the Nitricil™ was used as the vehicle control.

Rectangular wounds measuring 10 mm×7 mm×0.5 mm deep were made in the paravertebral and thoracic area of three animals. The wounds were separated from one another by 15 mm of unwounded skin. A 25 µl suspension containing $10^6$ cfu/ml of *Pseudomonas aeruginoas* was inoculated into each wound. All wounds were then covered with a polyurethane film dressing (Tegaderm; 3M, St. Paul, Minn.) within 30 minutes of inoculation and allowed to stay in place for 48 hours.

After 48 hours, the polyurethane film dressings were removed and three of the wounds were recovered for baseline bacterial counts. The remaining wounds were divided into four groups of eight wounds each, treated with ≅200 mg to cover wounded area and surrounding unwounded skin. The treatments were spread out gently with a sterile Teflon spatula and redressed with a film dressing.

Dressings were replaced daily after treatment application. Four wounds from each group were recovered prior to daily dressing changes as described in the "Recovery Section" below beginning on day 4 after wounding.

Three wounds were cultured 48 hours after inoculation for baseline enumeration of bacteria. Four wounds for each treatment group were recovered after treatment on days 4 and 7. To recover bacteria from the wounds, a sterile surgical steel cylinder (22 mm inside diameter) was placed around the wound area. One (1) ml of all purpose neutralizer solution was pipetted into the cylinder and the site was scrubbed with a sterile Teflon spatula for 30 seconds.

Serial dilutions were made from all culture samples and the extent of microbiological contamination assessed using the Spiral Plater System (Spiral Biotech, Norwood, Mass.). Pseudomonas Agar-base with CN supplement was used to isolate P. aeruginosa from the wounds. All plates were incubated aerobically overnight (24 hours) at 37° C., after which the number of viable colonies were counted.

Table 8 shows the results of the counts at Day 4 and Day 7 for the 2% and 4% ointment formulations, the vehicle control and an untreated control. As seen in Table 8, both the 2% and the 4% ointments achieved significant pathogen reduction by day 7.

TABLE 8

Ointment efficacy against *Pseudomonas areuginosa*.

| N = 12 | Counts (Log CFU/ml) | | | Reduction | | % Reduction | |
|---|---|---|---|---|---|---|---|
| *Pseudomonas areuginosa* | Day 0 | Day 4 | Day 7 | Day 4 | Day 7 | Day 4 | Day 7 |
| Baseline | 8.63 | | | | | | |
| 2% Ointment | | 7.62 | 4.92 | 1.01 | 3.71 | 90.2276% | 99.9805% |
| 4% Ointment | | 6.84 | 3.39 | 1.79 | 5.24 | 98.3782% | 99.9994% |
| Vehicle | | 8.62 | 7.07 | 0.01 | 1.56 | 2.2763% | 97.2458% |
| Untreated Control | | 9.26 | 8.48 | −0.63 | 0.15 | −326.5795% | 29.2054% |

Example 5

The formulations of Example 4 were also tested for efficacy against *Staphylococcus aureus* MRSA in the same porcine animal models utilizing 2 animals. The experimental procedure was as described in Example 4 except for the change in challenge pathogen. Table 9 shows the results for Days 4 and 7 for the 2% ointment, the 4% ointment, the vehicle control and the untreated control. As seen in Table 9, both the 2% and the 4% ointments prevented pathogen growth and reduced the counts by day 7.

TABLE 9

Ointment efficacy against *Staphylococcus aureus* MRSA

| N = 8 | | | | | | | |
|---|---|---|---|---|---|---|---|
| *Staphylococcus aureus* | Counts (Log CFU/ml) | | | Log Reduction | | % Reduction | |
| MRSA | Day 0 | Day 4 | Day 7 | Day 4 | Day 7 | Day 4 | Day 7 |
| Baseline | 8.87 | | | | | | |
| 2% Ointment | | 7.93 | 6.97 | 0.7 | 1.66 | 88.5185% | 98.7411% |
| 4% Ointment | | 7.54 | 6.44 | 1.09 | 2.19 | 95.3226% | 99.6285% |
| Vehicle | | 9.01 | 8.21 | −0.38 | 0.42 | −38.0384% | 78.1224% |
| Untreated Control | | 9.67 | 8.86 | −1.04 | −0.23 | −530.9573% | 2.2763% |

Example 6

A nitric oxide releasing macromolecular compound (Nitricil™ NVN1) comprising MAP3 was fabricated as described in United States Patent Application Publication No. 2009/0214618 and in PCT Patent Application Number PCT/US12/22048, filed Jan. 20, 2012, entitled "Temperature Controlled Sol-Gel Co-Condensation," the disclosures of which are incorporated herein by reference as if set forth in their entirety. The resulting macromolecular particles were ball milled to provide an average particle size of from 8 to 10 μm to provide an active pharmaceutical ingredient (API).

Figure 5:
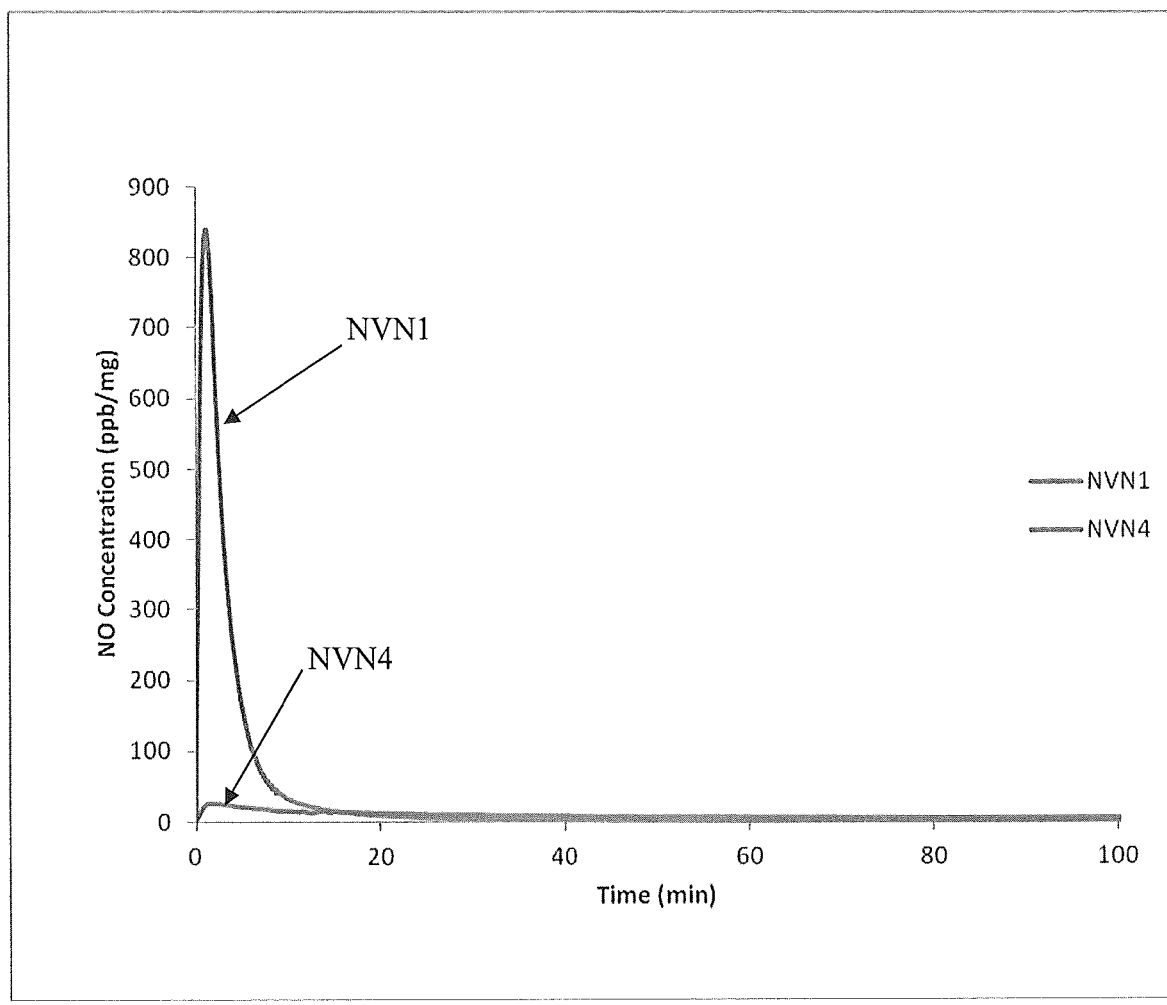
FIG. 5 shows a graph of the release profiles of two types of Nitricil™, NVN1 and NVN4, ointments according to some embodiments of the present invention under physiological conditions.

FIG. 5 is a graph of the release profiles for Nitricil™ NVN1 and NVN4 at pH 7.4 and 37° C. for the first 200 minutes of release. Nitricil™ NVN4 is a nitric oxide releasing macromolecular compound comprising AEP3/TEOS in a 1:1 ratio, and was fabricated as described in United States Patent Application Publication No. 2009/0214618 and in PCT Patent Application Number PCT/US12/22048, filed Jan. 20, 2012, entitled "Temperature Controlled Sol-Gel Co-Condensation" to provide an API. The overall release kinetics of Nitricil™ NVN1 are provided in Table 10 below.

TABLE 10

Half Life and Potency of Nitricil ™ NVN1 at pH 7.4 and 37° C.

| Compound | Half Life | Potency |
| --- | --- | --- |
| Nitricil ™ NVN1 | 2.3 minutes | 4.9 μmol/mg |

Nitricil™ NVN1 was formulated into two finished dosage forms of an ointment as set forth in Table 11.

TABLE 11

Nitricil ™ NVN1 ointment formulations.

| Component | 0.2% NVN1 | 2% NVN1 |
| --- | --- | --- |
| Mineral Oil, USP | 74.8 | 73.0 |
| Captex 300 | 10.0 | 10.0 |
| Miglyol 840 | 10.0 | 10.0 |
| Cab-o-sil M5P | 5.0 | 5.0 |
| Nitricil ™ NVN1 | 0.2 | 2.0 |
| Total | 100.0 | 100.0 |

The placebo ointment was formulated with the weight of the API being replaced by increasing the amount of mineral oil.

Example 7

BALB/c derived male mice, weighing 22±2 g, were provided by BioLasco Taiwan (under Charles River Laboratories Technology Licensee). The animals were housed in Individually Ventilated Cages Racks (IVC Racks, 36 Mini Isolator systems) under clean area throughout the experiment. Every 5 mice were kept in an animal cage (in cm, 26.7 length×20.7 width×14.0 height) sterilized with autoclave and maintained under controlled temperature (20-24° C.) and humidity (50%-80%) with 12-hour light/dark cycles. The animals were given free access to sterilized standard lab chow [MF-18 (Oriental Yeast Co., Ltd. Japan)] and sterile tap water ad libitum. All aspects of this work, i.e., housing, experimentation and disposal of animals, w performed in general accordance with the Guide for the Care and Use of Laboratory Animals (National Academy Press, Washington, D. C., 2010).

Groups of 5 BALB/c male mice weighing 22±2 g were used. The animals were sensitized by application of oxazolone (100 μL, 1.5% in acetone) to their preshaved abdominal surface. Seven days later, test substances (20 mg/ear) and vehicle (20 μL/ear) were applied topically to the anterior and posterior surfaces of the right ear 30 min before and 15 min after oxazolone (1%, 20 μL/ear) challenge. Ear swelling was measured with a Dyer model micrometer gauge at 24 hours after oxazolone challenge as an index of inflammation. Ear edema was calculated by subtracting the thickness of the left ear (normal control) from the right ear (treated ear). Percent inhibition was calculated according to the formula: (Ic−It)/Ic×100, where Ic and It refers to increase of ear thickness (mm) in control and treated mice, respectively. One-way ANOVA and Dunnett's test were used to determine statistical significance between vehicle control and treated groups. Significance is set at P<0.05.

Test articles (0.2% and 2% Nitricil™ NVN1 Ointment) described in Example 6 were evaluated for possible anti-inflammatory activity in the oxazolone-induced ear swelling assay in BALB/c mice, a model of allergic contact dermatitis. Test substances and vehicles were each administered topically (TOP) at 30 minutes before and 15 minutes after challenge with the second application of oxazolone. Effects of the test substances on ear swelling were measured 24 hours later and the results are summarized in Table 12 below.

TABLE 12

In vivo anti-inflammatory efficacy of NO-releasing compositions

| | | | Ear Swelling | |
| --- | --- | --- | --- | --- |
| Treatment | Route | Dose | % Inhibition (vs. Vehicle A) | % Inhibition |
| Vehicle A (acetone/ethanol: 1/1) | TOP | 20 μL/ear × 2 | — | — |
| Dexamethasone | TOP | 0.3 mg/ear × 2 | 85* | — |
| Placebo Ointment | TOP | 20 mg/ear × 2 | −17 | (vs. Placebo Ointment) |
| 2% Nitricil ™ NVN1 Ointment | TOP | 20 mg/ear × 2 | −4 | 11 |
| 0.2% Nitricil ™ NVN1 Ointment | TOP | 20 mg/ear × 2 | −11 | 5 |

Note:
Negative values indicate no inhibition or stimulation.
One-way ANOVA and Dunnett's test were used to ascertain difference between vehicle control (or respective placebo control) and treated groups.
*P < 0.05, vs. Vehicle A or respective placebo control.

Topical administration of 0.2% and 2% Nitricil™ NVN1 Ointment were not associated with significant inhibition vs. the vehicle control A (acetone/ethanol: 1/1) and placebo ointment. Placebo ointment treatment did not exhibit a significant effect on oxazolone-induced ear swelling. Dexamethasone (0.1 mg/ear×2), the positive control, was associated with significant inhibition of the oxazolone-induced ear swelling.

Example 8

Using a cold process, ointment formulations were prepared as set forth in Table 13. These formulations were selected for scale-up.

TABLE 13

Nitricil ™ NVN1 Ointment Formulations (TO-007 and TO-008).

| Component | % w/w TO-007 | | | | | | | | TO-008 | | |
|---|---|---|---|---|---|---|---|---|---|---|---|
| CrodabaseSQ | 61.4 | 61.3 | 61.0 | 61.0 | 60.0 | 58.0 | 52.0 | 45.0 | 60.0 | 60.0 | 60.0 |
| Miglyol 812 | 12.0 | 12.0 | 12.0 | 12.0 | 12.0 | 12.0 | 12.0 | 12.0 | 12.0 | 12.0 | 12.0 |
| Hexylene glycol | 8.0 | 8.0 | 8.0 | 8.0 | 8.0 | 8.0 | 8.0 | 8.0 | 8.0 | 8.0 | 8.0 |
| Light Mineral Oil | 8.5 | 8.5 | 8.5 | 8.0 | 8.0 | 6.0 | 6.0 | 5.0 | 15.0 | 13.0 | 11.0 |
| Softigen 767 | 10.0 | 10.0 | 10.0 | 10.0 | 10.0 | 10.0 | 10.0 | 10.0 | 5.0 | 5.0 | 5.0 |
| Nitricil ™ NVN1 | 0.1 | 0.2 | 0.5 | 1.0 | 2.0 | 6.0 | 12.0 | 20.0 | 2.0 | 4.0 | 8.0 |

The lab-scale process used during development of the formulations provided in Table 13 was scaled-up to the 5.5-kg scale using a Ross Dual Shaft Mixer, Model No.: CDA-2 with an 8-L mixing vessel. The agitation and homogenization system contained two independently driven top-entering agitators, as described below:

1. A Three-Wing Anchor Agitator driven at a speed range of approximately 23-225 rpm. The anchor is designed with a triangular cross section and includes fixed Teflon scrapers for wiping the sidewall and bottom of mix can.
2. A High-Speed Disperser, 2" diameter blade, driven at a speed range of approximately 1,000-10,000 rpm.

Figure 6:
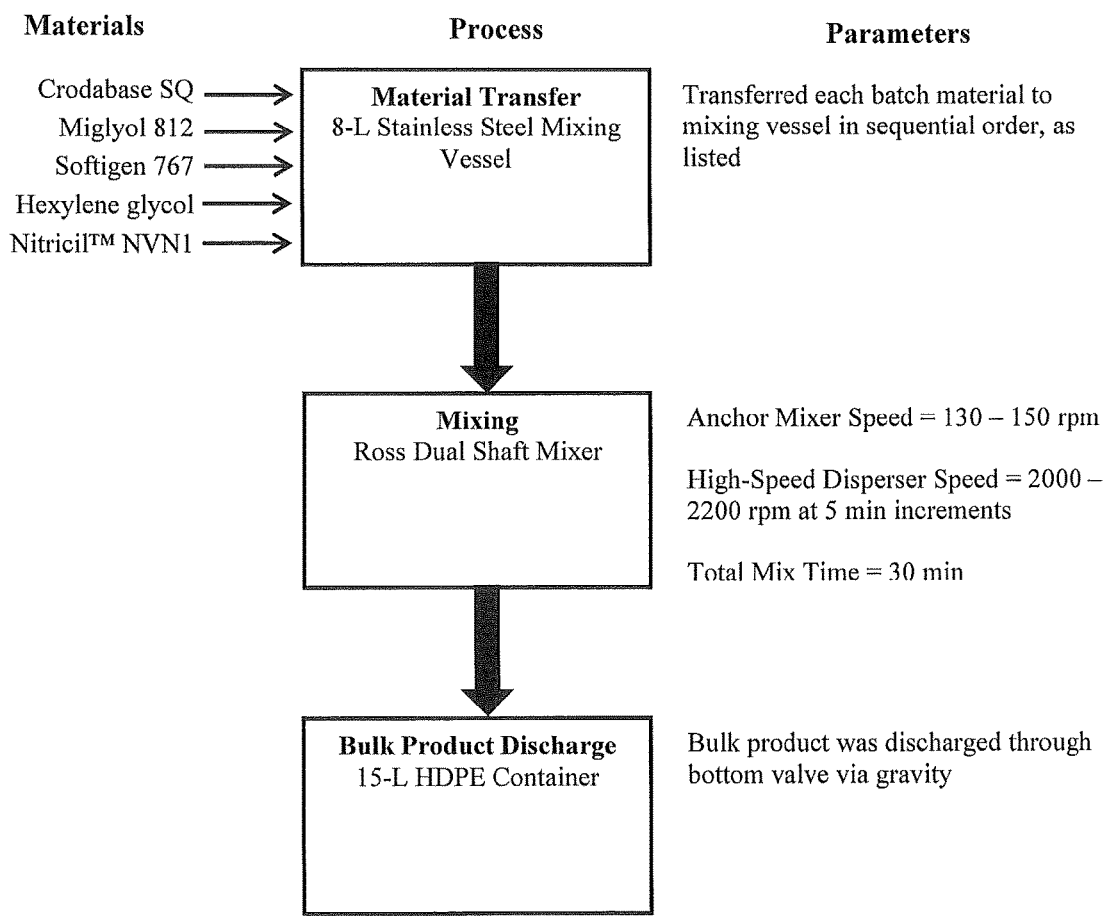
FIG. 6 shows a process flow diagram for the 5.5-kg scale manufacture of an ointment according to some embodiments of the present invention.

Four batches of ointment were manufactured to determine the order of material addition, as well as suitable mixing speeds (anchor agitator and high-speed disperser), and mixing times for the small-scale process. A summary of the development batch formulations is provided in Table 14 and the process flow diagram for the manufacture is provided in FIG. 6.

TABLE 14

Batch formulas for topical ointments.

| | Batch 1 Placebo Ointment | | Batch 2 2% Ointment | | Batch 3 2% Ointment | | Batch 3 20% Ointment | |
|---|---|---|---|---|---|---|---|---|
| Component | % w/w | Batch Wt. (g) | % w/w | Batch Wt. (g) | % w/w | Batch Wt. (g) | % w/w | Batch Wt. (g) |
| Crodabase SQ Croda, Lot# 0000630349 | 60.0 | 1800.0 | 60.0 | 1800.0 | 60.0 | 1800.0 | 52.0 | 1690.0 |
| Light Mineral Oil, NF Spectrum, Lot# ZI0511 | 15.0 | 450.0 | 13.0 | 390.0 | 13.0 | 390.0 | 3.0 | 650.0 |
| Miglyol 812 Sasol, Lot# 110807 | 12.0 | 360.0 | 12.0 | 360.0 | 12.0 | 360.0 | 12.0 | 390.0 |
| Hexylene glycol, NF Haltermann, Lot# ME08T304 | 8.0 | 240.0 | 8.0 | 240.0 | 8.0 | 240.0 | 8.0 | 260.0 |
| Softigen 767 Sasol, Lot# 106445 | 5.0 | 150.0 | 5.0 | 150.0 | 5.0 | 150.0 | 5.0 | 162.5 |
| Nitricil ™ NVN1 Novan, Batch# 11-23-17M | | | 2.0 | 60.0 | 2.0 | 60.0 | 20.0 | 97.5 |
| Total | 100.0 | 3000.0 | 100.0 | 3000.0 | 100.0 | 3000.0 | 100.0 | 3250.0 |

The analytical results of the batches are provided in Tables 15 and 16.

TABLE 15

Analytical results for placebo ointment.

| Test | Proposed Specification | Method Reference | Result |
|---|---|---|---|
| Appearance | Colorless to Off-white, Translucent to Opaque Ointment | METH-014 | White, opaque gel |
| Absence of NVN1 by HPLC | NVN1 is absent from the sample chromatogram | METH-058 | Conforms |
| Moisture Content | Report Value, % w/w | METH-003 | 0.2 |
| Apparent pH | Report Value | METH-006 | 6.4 |

TABLE 16

Analytical results for the 2%, 6%, 12%, and 20% Nitricil ™ NVN1 Ointments.

| Test | Proposed Specification | Method Reference | Result 2% (1203301-15) | 6% (1203901-15) | 12% (1203401-15) | 20% (1203501-15) |
|---|---|---|---|---|---|---|
| Appearance | White to Off-white Opaque Ointment | METH-014 | Off-white, Opaque Ointment | Off-white, Opaque Ointment | Off-white, Opaque Ointment | Off-white, Opaque Ointment |
| NVN1 ID (NOA) | Conforms to presence of NVN1000 by presence of nitric oxide | METH-020 | Conforms | Conforms | Conforms | Conforms |
| NVN1 ID (HPLC) | Conforms to presence of NVN1000 by retention time comparison | METH-058 | Conforms | Conforms | Conforms | Conforms |
| NO Content (NOA) | 2% . . . 0.27-0.33% NO 6% . . . 0.77-1.04% NO 12% . . . 1.62-1.98% NO 20% . . . 2.70-3.30% NO | METH-020 | 0.29% | 0.80% | 1.68% | 3.11% |
| NVN1 Assay (HPLC) | 80.0-120.0% LC | METH-058 | 89.3% | 92.8% | 104.5% | 105.4% |
| Moisture Content | Report Result, % w/w | METH-036 | 0.3% | 0.4% | 0.7% | 0.9% |
| Apparent pH | Report Value | METH-039 | 11.4 | 11.7 | 11.7 | 11.7 |

Example 9

A Nitricil™ ointment was evaluated in BALB/c mice to determine the potential anti-inflammatory properties of the Nitricil™ ointment in vivo. BALB/c derived male mice, weighing 22±2 g, were provided by BioLasco Taiwan (under Charles River Laboratories Technology Licensee). The animals were housed in Individually Ventilated Cages Racks (IVC Racks, 36 Mini Isolator systems) under clean area throughout the experiment. Every 5 mice were kept in an animal cage (in cm, 26.7 length×20.7 width×14.0 height) sterilized with autoclave and maintained under controlled temperature (20-24° C.) and humidity (50%-80%) with 12-hour light/dark cycles. The animals were given free access to sterilized standard lab chow [MF-18 (Oriental Yeast Co., Ltd. Japan)] and sterile tap water ad libitum. All aspects of this work, i.e., housing, experimentation and disposal of animals, were performed in general accordance with the Guide for the Care and Use of Laboratory Animals (National Academy Press, Washington, D. C., 2011).

Nitricil™ topical ointment (1% and 4%) and placebo ointment were tested in this study. The composition of the Nitricil™ topical ointment formulations and placebo ointment are provided in Table 17. Dexamethasone (0.1 mg/ear) was used as a positive control. Dexamethasone is a potent glucocorticoid steroid that is used to treat various inflammatory and autoimmune disorders.

TABLE 17

Composition of ointment formulations used in this study.

| | % w/w | | |
|---|---|---|---|
| Component | Placebo | 1% | 4% |
| Mineral Oil and Polyethylene Crodabase SQ, Croda | 61.0 | 55.5 | 54.0 |
| Medium Chain Triglycerides, NF Miglyol 812, Sasol | 12.0 | 12.0 | 12.0 |
| Hexylene glycol Fluka | 8.0 | 8.0 | 8.0 |
| Light Mineral Oil, NF Spectrum | 9.0 | 13.5 | 12.0 |
| PEG-6-Capric/Caprylic Glyceride, Ph.Eur. Softigen 767, Sasol | 10.0 | 10.0 | 10.0 |
| Nitricil ™ NVN1 Novan, Inc., Batch# 1200601 | — | 1.0 | 4.0 |

The test system used was a 7-day oxazolone-induced ear swelling assay. Oxazolone-induced ear swelling is useful as a model of inflammation. Oxazolone is an allergen that induces delayed type hypersensitivity, and is therefore most useful as a model of inflammation driven by the adaptive immune response (e.g., allergic contact dermatitis, psoriasis, etc). In this assay, mice (5 per group) were sensitized to oxazolone (100 μL, 1.5% in acetone) through one topical application of oxazolone to their preshaved abdomen surface. Seven days later, animals were challenged with a second application of oxazolone to the ear. Test articles (20 mg/mouse) and vehicle (20 μL/ear) were administered topically (TOP) to the anterior and posterior surfaces of the right ear 30 minutes before and 15 minutes after the second oxazolone (1%, 20 μL/ear) challenge (elicitation phase). Ear swelling was measured with a Dyer model micrometer gauge at 24 hours after oxazolone challenge as an index of inflammation. Ear edema was calculated by subtracting the thickness of the left ear (normal control) from the right ear (treated ear) (Table 18). An additional group was treated with dexamethasone, a known anti-inflammatory agent, (positive control) to verify assay validity.

Percent inhibition was calculated according to the formula: (Ic–It)/Ic×100, where Ic and It refer to increase of ear thickness (mm) in control and treated mice, respectively. One-way ANOVA and Dunnett's test were used to determine statistical significance between vehicle control and treated groups. Significance is set at $P<0.05$.

TABLE 18

Treatment information and swelling results.

| Treatment | Route | Dose | Net Swelling on Right Ear (Mean ± SEM, × 0.01 mm) |
|---|---|---|---|
| Vehicle (Acetone:Ethanol/1:1) | TOP | 20 μL/ear × 2 | 22.6 ± 1.2 |
| Dexamethasone | TOP | 0.1 mg/ear × 2 | 3.2 ± 0.4* |
| Placebo ointment | TOP | 20 mg/ear × 2 | 23.2 ± 1.5 |
| 1% Nitricil ™ NVN1 Topical Ointment | TOP | 20 mg/ear × 2 | 9.8 ± 1.2*,† |
| 4% Nitricil ™ NVN1 Topical Ointment | TOP | 20 mg/ear × 2 | 9.2 ± 0.6*,† |

Note:
One-way ANOVA and Dunnett's test were used to ascertain difference between placebo/vehicle control and treated groups.
*$P < 0.05$, vs. Vehicle (Acetone:Ethanol/1:1).
†$P < 0.05$, vs. Placebo ointment.

Topical administration of 1% Nitricil™ NVN1 Topical Ointment and 4% Nitricil™ NVN1 Topical Ointment were both associated with significant ($P<0.05$) inhibition of oxazolone-induced ear swelling versus both the vehicle control (acetone/ethanol: 1/1) and placebo ointment. The 1% Nitricil™ NVN1 Topical Ointment inhibited ear swelling by 57% versus acetone/ethanol vehicle and by 58% versus placebo ointment. The 4% Nitricil™ NVN1 Topical Ointment inhibited ear swelling by 59% versus acetone/ethanol vehicle and by 60% versus placebo ointment. The placebo ointment had no effect on ear swelling relative to the acetone/ethanol vehicle. Dexamethasone (positive control) inhibited ear swelling by 86% relative to the acetone/ethanol vehicle.

Topical administration of Nitricil™ topical ointment at 1% and 4% caused significant ($P<0.05$) inhibition of the oxazolone-induced ear swelling in mice compared to the placebo ointment control or vehicle (Acetone/Ethanol:1/1). Thus, Nitricil™ topical ointment 1% and 4% both significantly inhibited inflammation in an in vivo model of allergic contact dermatitis. The 4% Nitricil™ NVN1 Topical Ointment was not significantly more effective than the 1% Nitricil™ NVN1 Topical Ointment under the conditions of this test. The placebo ointment group did not have any effect relative to vehicle control (Acetone/Ethanol:1/1). Dexamethasone (0.1 mg/mouse×2), the positive control, was associated with significant inhibition of the oxazolone-induced ear swelling in mice. Table 19 shows a comparison of the percent inhibition of the oxazolone-induced ear swelling results from this study, the study described in Example 7, and a subsequent study with Nitricil™ ointment formulations as described in Example 8 to an ethanol/acetone vehicle formulation or a placebo formulation. For the Nitricil™ NVN4 ointment formulations, the formulations were similar to those provided in Example 8 for the Nitricil™ NVN1 ointment formulations with minor adjustments made to the light mineral oil to account for the difference in the amount of Nitricil™ in the formulation.

TABLE 19

Comparison of the percent inhibition of the oxazolone-induced ear swelling results from various studies.

| | | % inhibition of oxazolone-induced ear swelling | |
|---|---|---|---|
| Example | Test Article | vs ethanol/ acetone | vs placebo formulation |
| 7 | Placebo Ointment | −17 | n/a |
| 7 | 0.2% Nitricil ™ NVN1 Ointment | −11 | 5 |
| 7 | 2% Nitricil ™ NVN1 Ointment | −4 | 11 |
| 9 | Placebo Ointment | −3 | n/a |
| 9 | 1% Nitricil ™ NVN1 Ointment | 57* | 58* |
| 9 | 4% Nitricil ™ NVN1 Ointment | 59* | 60* |
| 8 | Placebo Ointment | 33* | n/a |
| 8 | 2.8% Nitricil ™ NVN4 Ointment | 43* | 14* |
| 8 | 5.6% Nitricil ™ NVN4 Ointment | 55* | 32* |
| 8 | 11.2% Nitricil ™ NVN4 Ointment | 61* | 42* |
| 8 | 2% Nitricil ™ NVN1 Ointment | 24* | −14 |
| 8 | 4% Nitricil ™ NVN1 Ointment | 57* | 36* |
| 8 | 8% Nitricil ™ NVN1 Ointment | 62* | 43* |

*Significant ($P < 0.05$) inhibition versus ethanol/acetone vehicle or placebo formulation.

Example 10

Wound Healing Study in a Porcine Partial-Thickness Wound Model

Using Nitricil™ NVN1 ointments, such as the TO-007 ointment formulations described in Example 8, partial thickness wounds were treated in a porcine model. Partial thickness wounds were treated with the following formulations: ointment formulations containing 0.1%, 0.5%, 1%, or 4% Nitricil™ NVN1, vehicle ointment, Tegaderm for standard occlusion as a positive control, or left air exposed as a negative control.

Figure 7:
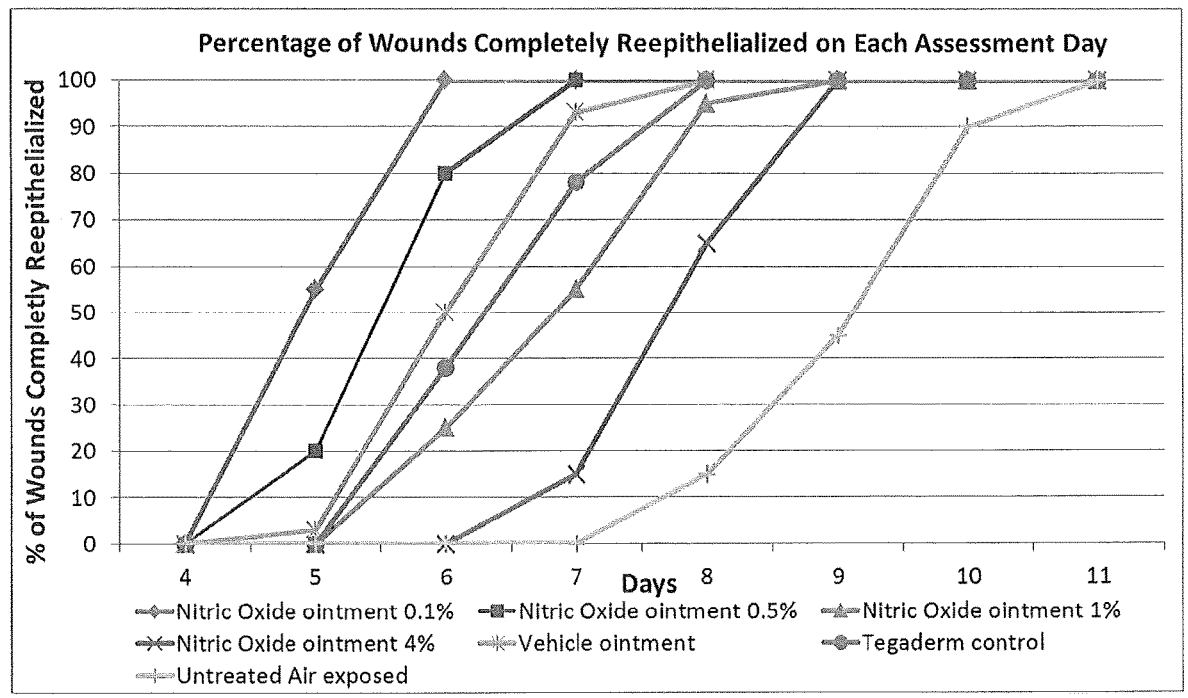
FIG. 7 shows a graph of the effect of nitric oxide-releasing Nitricil™ NVN1 ointment on wound re-epithelialization.

Results from the eight-animal wound healing study are shown in FIG. 7. The lower doses, 0.1% and 0.5% Nitricil™ NVN1 ointment, demonstrated much faster rates of re-epithelialization. All 20 wounds in the lowest dose (0.1%) were completely healed by Day 6, 2 full days faster than the corresponding ointment vehicle or the Tegaderm occlusive standard of care. Even though this data was not collected in a thermal injury model, it clearly demonstrates the ability of nitric oxide to stimulate faster healing.

Two biopsies were taken from all animals in each treatment group on Day 2, 4, and 7 post wounding. Wedge biopsies for histology were obtained through the center of the wounds including normal adjacent skin on both sides. Punch biopsies were taken from the other half of the wound for RNA isolation and subsequent RT-PCR analysis.

Figure 8:
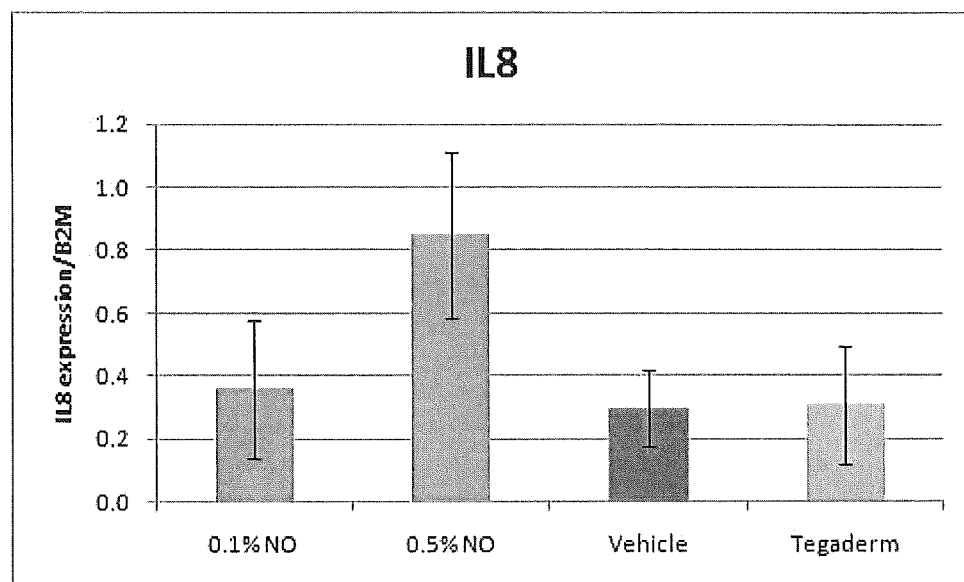
FIG. 8 shows a graph of the expression levels of IL-8 in wound tissue measured by qPCT in wounds treated with 0.1% and 0.5% Nitricil™ NVN1, vehicle, and Tegaderm.

No differences in epithelial thickness were observed for any of the treatment groups, showing a regulated healing process and no overproliferation of cells in the epithelium. Wounds treated with 0.5% Nitricil™ NVN1 ointment expressed an elevated level of IL-8 mRNA on Day 2 compared to the other treatment groups (FIG. 8). Expression of IL-8, a neutrophil chemoattractant, was significantly induced in wounds following 2 days of treatment with 0.5%

Figure 9:
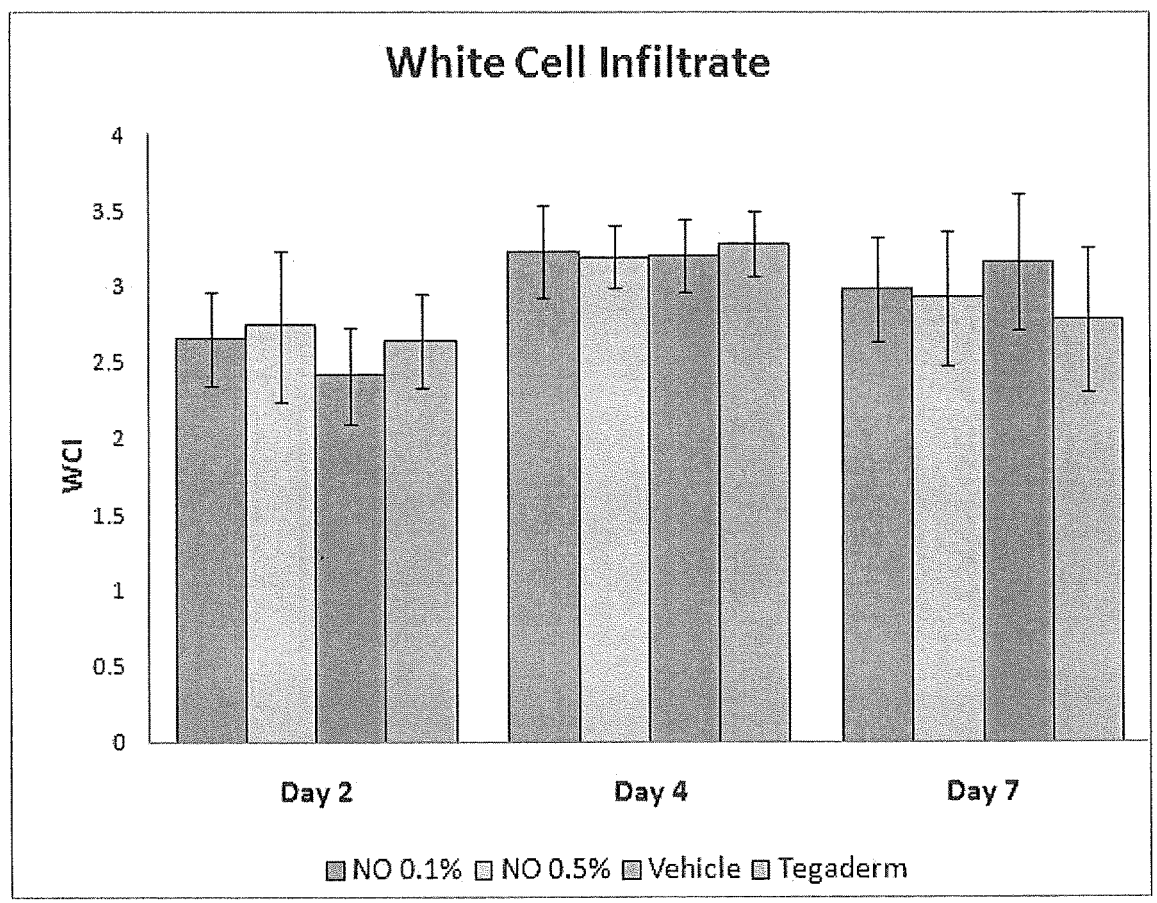
FIG. 9 shows a graph of the white cell infiltrate assessed by the presence and amount of subepithelial mixed leukocytic infiltrates.

Nitricil™ NVN1 ointment (p≤0.05). Nitric oxide can activate the IL-8 promoter and IL-8 in turn can suppress the expression of iNOS in neutrophils. This signaling effect was enough to promote healing but did not facilitate over recruitment of neutrophils and cause a sustained inflammatory response (FIG. 9). The white cell infiltrate measured via histology was not statistically different for any of the treatments.

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A nitric oxide (NO)-releasing pharmaceutical composition, the NO-releasing pharmaceutical composition comprising:
    a hydrophobic base present in the NO-releasing pharmaceutical composition at a concentration from about 35% to about 90% by weight of the NO-releasing pharmaceutical composition;
    an amphiphilic compound present in the NO-releasing pharmaceutical composition at a concentration from about 1% to about 30% by weight of the NO-releasing pharmaceutical composition, wherein the amphiphilic compound is a polyethylene glycol (PEG) caprylic/capric glyceride;
    water at a concentration of less than about 2% by weight of the NO-releasing pharmaceutical composition; and
    an active pharmaceutical ingredient, wherein the active pharmaceutical ingredient consists of diazeniumdiolate-functionalized polysiloxane macromolecules that are NO-releasing co-condensed silica particles.

2. The NO-releasing pharmaceutical composition of claim 1, wherein the amphiphilic compound has a hydrophilic-lipophilic balance (HLB) value of 12 to 20.

3. The NO-releasing pharmaceutical composition of claim 1, wherein the amphiphilic compound absorbs moisture and does not substantially absorb vaporous moisture.

4. The NO-releasing pharmaceutical composition of claim 1, wherein the hydrophobic base comprises at least one of mineral oil and a hydrophobic polymer.

5. The NO-releasing pharmaceutical composition of claim 1, further comprising a cosolvent and the cosolvent is present in the NO-releasing pharmaceutical composition at a concentration from about 1% to about 30% by weight of the NO-releasing pharmaceutical composition.

6. The NO-releasing pharmaceutical composition of claim 5, wherein the cosolvent comprises a fatty acid ester.

7. The NO-releasing pharmaceutical composition of claim 1, further comprising a humectant and the humectant is present in the NO-releasing pharmaceutical composition at a concentration from about 1% to about 25% by weight of the NO-releasing pharmaceutical composition.

8. The NO-releasing pharmaceutical composition of claim 7, wherein the humectant comprises a polyhydric alcohol.

9. The NO-releasing pharmaceutical composition of claim 1, wherein the diazeniumdiolate-functionalized polysiloxane macromolecules are present in the composition at a concentration of up to about 70% by weight of the NO-releasing pharmaceutical composition.

10. The NO-releasing pharmaceutical composition of claim 1, wherein the co-condensed silica particles have a mean particle size of less than about 10 μm.

11. The NO-releasing pharmaceutical composition of claim 1, wherein the NO-releasing pharmaceutical composition is an ointment.

12. The NO-releasing pharmaceutical composition of claim 1, wherein the amphiphilic compound is present in the NO-releasing pharmaceutical composition at a concentration from about 1% to less than 5% by weight of the NO-releasing pharmaceutical composition.

13. The NO-releasing pharmaceutical composition of claim 1, wherein the hydrophobic base comprises a hydrophobic hydrocarbon polymer and mineral oil.

14. The NO-releasing pharmaceutical composition of claim 1, wherein the amphiphilic compound comprises a PEG-6-caprylic/capric glyceride.

15. The NO-releasing pharmaceutical composition of claim 1, wherein the hydrophobic base comprises a polysiloxane.

16. A pharmaceutical composition for topical delivery of nitric oxide, the composition comprising:
    an active pharmaceutical ingredient;
    a hydrophobic base comprising:
        a first hydrophobic base present in the composition at a concentration from 35% to 80% by weight of the composition, wherein the first hydrophobic base comprises a hydrophobic hydrocarbon polymer; and
        a second hydrophobic base present in the composition at a concentration from 1% to 20% by weight of the composition, wherein the second hydrophobic base is mineral oil; and
    an amphiphilic compound present in the composition at a concentration from 1% to 20% by weight of the composition, wherein the amphiphilic compound is a polyethylene glycol (PEG) caprylic/capric glyceride;
    wherein the active pharmaceutical ingredient consists of diazeniumdiolate-functionalized polysiloxane macromolecules that are nitric oxide (NO)-releasing co-condensed silica particles and the diazeniumdiolate-functionalized polysiloxane macromolecules are present in the composition at a concentration of up to 35% by weight of the composition, and
    wherein the composition has a NO content in a range of 0.27% to 3.30% by weight of the composition.

17. The pharmaceutical composition of claim 16, wherein water is present in the composition at a concentration of less than about 2%.

18. The pharmaceutical composition of claim 16, wherein the amphiphilic compound comprises a PEG-6-caprylic/capric glyceride.

19. The pharmaceutical composition of claim 16, wherein mineral oil is present in the composition at a concentration from 1% to 9% by weight of the composition, and the PEG caprylic/capric glyceride is present in the composition at a concentration from about 1% to less than 5% by weight of the composition.

20. The pharmaceutical composition of claim 16, wherein mineral oil is present in the composition at a concentration from 10% to 20% by weight of the composition, and the PEG caprylic/capric glyceride is present in the composition at a concentration from about 1% to less than 5% by weight of the composition.

21. A method of treating the skin of a subject, the method comprising topically administering the NO-releasing pharmaceutical composition of claim 1 in an amount effective to treat the skin of a subject.

22. The method of claim 21, further comprising contacting water to the pharmaceutical composition before, after, and/or during the step of topically administering the composition.

* * * * *

UNITED STATES PATENT AND TRADEMARK OFFICE
CERTIFICATE OF CORRECTION

PATENT NO. : 11,077,194 B2
APPLICATION NO. : 14/381370
DATED : August 3, 2021
INVENTOR(S) : Ryan Doxey Page 1 of 1

It is certified that error appears in the above-identified patent and that said Letters Patent is hereby corrected as shown below:

On the Title Page

(56) References Cited, FOREIGN PATENT DOCUMENTS, Page 2, Column 2, Line 15:
Please correct "WO 03/09539 11/2003" to read -- WO 03/095398 11/2003 --

(56) References Cited, FOREIGN PATENT DOCUMENTS, Page 2, Column 2, Line 72:
Please correct "WO 2018189887 10/2018" to read -- WO 2018189687 10/2018 --

Signed and Sealed this
First Day of March, 2022

Drew Hirshfeld
*Performing the Functions and Duties of the
Under Secretary of Commerce for Intellectual Property and
Director of the United States Patent and Trademark Office*